(12) United States Patent
Melder et al.

(10) Patent No.: US 8,678,046 B2
(45) Date of Patent: Mar. 25, 2014

(54) APPARATUS AND METHODS FOR LOADING A DRUG ELUTING MEDICAL DEVICE

(75) Inventors: Robert Melder, Santa Rosa, CA (US); Barry Wohl, Cambridge, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 770 days.

(21) Appl. No.: 12/884,501

(22) Filed: Sep. 17, 2010

(65) Prior Publication Data

US 2012/0067454 A1    Mar. 22, 2012

Related U.S. Application Data

(60) Provisional application No. 61/244,050, filed on Sep. 20, 2009.

(51) Int. Cl.
*B65B 3/04* (2006.01)

(52) U.S. Cl.
USPC .................................. 141/18; 141/2; 141/284

(58) Field of Classification Search
USPC ........ 623/1.42, 1.43; 427/2.1, 2.25, 230, 231; 141/2, 18, 284
See application file for complete search history.

(56) References Cited

U.S. PATENT DOCUMENTS

| | | | |
|---|---|---|---|
| 2,153,936 A | 4/1939 | Owens et al. |
| 4,531,933 A | 7/1985 | Norton et al. |
| 4,643,716 A | 2/1987 | Drach |
| 4,720,384 A | 1/1988 | DiLuccio et al. |
| 4,763,647 A | 8/1988 | Gambale |
| 4,800,082 A | 1/1989 | Karbowski et al. |
| 4,800,882 A | 1/1989 | Glanturco |
| 4,813,925 A | 3/1989 | Anderson, Jr. et al. |
| 4,886,062 A | 12/1989 | Wiktor |
| 4,913,683 A | 4/1990 | Gregory |
| 5,019,090 A | 5/1991 | Pinchuk |
| 5,063,935 A | 11/1991 | Gambale |
| 5,133,732 A | 7/1992 | Wiktor |
| 5,154,705 A | 10/1992 | Fleischhacker et al. |

(Continued)

FOREIGN PATENT DOCUMENTS

| | | |
|---|---|---|
| EP | 836839 A2 | 10/1997 |
| EP | 1600534 | 11/2005 |

(Continued)

OTHER PUBLICATIONS

U.S. Appl. No. 09/716,146, Nov. 17, 2000, Boyle.

(Continued)

*Primary Examiner* — Jason K Niesz

(57) ABSTRACT

Methods and apparatus are disclosed for loading a therapeutic substance or drug within a lumenal space of a hollow wire having a plurality of side openings along a length thereof that forms a hollow drug-eluting stent with a plurality of side drug delivery openings. Loading a drug within the lumenal space of the hollow stent includes a drug filling step, in which the drug is mixed with a solvent or dispersion medium. The lumenal space may be filled with the drug solution or suspension in a reverse fill process and/or a forward fill process. After the drug filling step, a solvent or dispersion medium extracting step is performed to extract the solvent or dispersion medium from within the lumenal space such that only the drug remains within the hollow stent. A stent cleaning step may be performed to an exterior surface of the hollow stent.

20 Claims, 24 Drawing Sheets

(56) References Cited

U.S. PATENT DOCUMENTS

| | | |
|---|---|---|
| 5,234,456 A | 8/1993 | Silvestrini |
| 5,306,250 A | 4/1994 | March et al. |
| 5,345,945 A | 9/1994 | Hodgson et al. |
| 5,536,274 A | 7/1996 | Neuss |
| 5,538,735 A | 7/1996 | Ahn |
| 5,569,197 A | 10/1996 | Helmus et al. |
| 5,605,162 A | 2/1997 | Mirzaee et al. |
| 5,630,840 A | 5/1997 | Mayer |
| 5,670,161 A | 9/1997 | Healy et al. |
| 5,782,903 A | 7/1998 | Wiktor |
| 5,795,318 A | 8/1998 | Wang et al. |
| 5,824,045 A | 10/1998 | Alt |
| 5,843,117 A | 12/1998 | Alt et al. |
| 5,882,335 A | 3/1999 | Leone et al. |
| 5,891,108 A | 4/1999 | Leone et al. |
| 5,902,266 A | 5/1999 | Leone et al. |
| 5,957,903 A | 9/1999 | Mirzaee et al. |
| 6,022,369 A | 2/2000 | Jacobson et al. |
| 6,063,101 A | 5/2000 | Jacobsen et al. |
| 6,071,305 A | 6/2000 | Brown et al. |
| 6,099,561 A | 8/2000 | Alt |
| 6,136,023 A | 10/2000 | Boyle |
| 6,248,190 B1 | 6/2001 | Stinson |
| 6,358,276 B1 | 3/2002 | Edwin |
| 6,478,778 B1 | 11/2002 | Jacobsen et al. |
| 6,497,709 B1 | 12/2002 | Heath |
| 6,558,422 B1 | 5/2003 | Baker et al. |
| 6,623,519 B2 | 9/2003 | Edwin |
| 6,641,607 B1 | 11/2003 | Hossainy et al. |
| 6,656,162 B2 | 12/2003 | Santini, Jr. et al. |
| 6,699,281 B2 | 3/2004 | Vallana et al. |
| 6,752,829 B2 | 6/2004 | Kocur et al. |
| 6,783,543 B2 | 8/2004 | Jang |
| 6,989,071 B2 | 1/2006 | Kocur et al. |
| 7,041,130 B2 | 5/2006 | Santini, Jr. et al. |
| 7,044,965 B1 | 5/2006 | Spielberg |
| 7,060,093 B2 | 6/2006 | Dang et al. |
| 7,101,392 B2 | 9/2006 | Heath |
| 7,122,048 B2 | 10/2006 | Dimatteo et al. |
| 7,135,039 B2 | 11/2006 | De Scheerder et al. |
| 7,288,084 B2 | 10/2007 | Li |
| 7,344,563 B2 | 3/2008 | Vallana et al. |
| 7,384,660 B2 | 6/2008 | Hossainy et al. |
| 7,575,593 B2 | 8/2009 | Rea et al. |
| 8,460,745 B2 * | 6/2013 | Mitchell et al. .............. 427/2.24 |
| 2002/0065548 A1 | 5/2002 | Birdsall et al. |
| 2002/0087209 A1 | 7/2002 | Edwin et al. |
| 2002/0103527 A1 | 8/2002 | Kocur et al. |
| 2002/0138048 A1 | 9/2002 | Tuch |
| 2003/0021825 A1 | 1/2003 | Pathak et al. |
| 2003/0068353 A1 | 4/2003 | Chen et al. |
| 2003/0125803 A1 | 7/2003 | Vallana et al. |
| 2003/0208256 A1 | 11/2003 | DiMatteo et al. |
| 2004/0006382 A1 | 1/2004 | Sohier |
| 2004/0018296 A1 | 1/2004 | Castro |
| 2004/0023339 A1 | 2/2004 | Karpas |
| 2004/0024449 A1 | 2/2004 | Boyle |
| 2004/0037889 A1 | 2/2004 | Richeal et al. |
| 2004/0106984 A1 | 6/2004 | Stinson |
| 2004/0133270 A1 | 7/2004 | Grandt |
| 2004/0148012 A9 | 7/2004 | Jang |
| 2005/0043783 A1 | 2/2005 | Amis et al. |
| 2005/0055080 A1 | 3/2005 | Istephanous et al. |
| 2005/0060020 A1 | 3/2005 | Jenson |
| 2005/0070996 A1 | 3/2005 | Dinh et al. |
| 2005/0080481 A1 | 4/2005 | Madda et al. |
| 2005/0145307 A1 | 7/2005 | Shireman et al. |
| 2005/0177226 A1 | 8/2005 | Banik et al. |
| 2005/0182390 A1 | 8/2005 | Shanley |
| 2005/0186241 A1 | 8/2005 | Boyle et al. |
| 2005/0208100 A1 | 9/2005 | Weber et al. |
| 2005/0272806 A1 | 12/2005 | Falotico et al. |
| 2005/0278016 A1 | 12/2005 | Welsh et al. |
| 2006/0004437 A1 | 1/2006 | Jayaraman |
| 2006/0064157 A1 | 3/2006 | Shanley |
| 2006/0122689 A1 | 6/2006 | Kocur et al. |
| 2006/0129231 A1 | 6/2006 | De Scheerder et al. |
| 2006/0147489 A1 | 7/2006 | Shanley et al. |
| 2006/0155369 A1 | 7/2006 | Edwin et al. |
| 2006/0200231 A1 | 9/2006 | O'Brien |
| 2006/0212109 A1 | 9/2006 | Sirhan et al. |
| 2006/0224234 A1 | 10/2006 | Jayaraman |
| 2006/0224237 A1 | 10/2006 | Furst et al. |
| 2007/0005124 A1 | 1/2007 | De Scheerder et al. |
| 2007/0027531 A1 | 2/2007 | Dimatteo et al. |
| 2007/0043423 A1 | 2/2007 | Grewe |
| 2007/0055352 A1 | 3/2007 | Naimark et al. |
| 2007/0061007 A1 | 3/2007 | Nolting |
| 2007/0112417 A1 | 5/2007 | Shanley et al. |
| 2007/0123805 A1 | 5/2007 | Shireman et al. |
| 2007/0168021 A1 | 7/2007 | Holmes, Jr. et al. |
| 2007/0173923 A1 | 7/2007 | Savage et al. |
| 2007/0219628 A1 | 9/2007 | Shanley et al. |
| 2007/0282419 A1 | 12/2007 | Hilaire et al. |
| 2008/0003251 A1 | 1/2008 | Zhou |
| 2008/0051882 A1 | 2/2008 | Rubin |
| 2008/0065201 A1 | 3/2008 | Li |
| 2008/0077233 A1 | 3/2008 | Diaz et al. |
| 2008/0183281 A1 | 7/2008 | Rea et al. |
| 2008/0188925 A1 | 8/2008 | Zhao |
| 2008/0195170 A1 | 8/2008 | Asgari |
| 2008/0195196 A1 | 8/2008 | Asgari |
| 2008/0234809 A1 | 9/2008 | Greenan |
| 2008/0249599 A1 | 10/2008 | Allen et al. |
| 2008/0255659 A1 | 10/2008 | Huang et al. |
| 2008/0276935 A1 | 11/2008 | Wang |
| 2008/0306579 A1 | 12/2008 | Dolan et al. |
| 2009/0024209 A1 | 1/2009 | Ozdil et al. |
| 2009/0024210 A1 | 1/2009 | Klocke et al. |
| 2009/0035351 A1 | 2/2009 | Berglund et al. |
| 2009/0061071 A1 | 3/2009 | McMorrow et al. |
| 2009/0093871 A1 | 4/2009 | Rea et al. |
| 2009/0132031 A1 | 5/2009 | Cook et al. |
| 2009/0157172 A1 | 6/2009 | Kokate et al. |
| 2009/0163995 A1 | 6/2009 | Shanley et al. |
| 2009/0192593 A1 | 7/2009 | Meyer et al. |
| 2009/0220612 A1 | 9/2009 | Perera |
| 2009/0228095 A1 | 9/2009 | Shanley et al. |
| 2009/0281615 A1 | 11/2009 | Kocur et al. |
| 2009/0312833 A1 | 12/2009 | Tittelbach et al. |
| 2009/0319026 A1 | 12/2009 | Meyer |
| 2010/0010621 A1 | 1/2010 | Klocke |
| 2010/0023115 A1 | 1/2010 | Robaina et al. |
| 2010/0036482 A1 | 2/2010 | Svrluga et al. |
| 2010/0057196 A1 | 3/2010 | Pathak |
| 2010/0070022 A1 | 3/2010 | Kuehling |
| 2010/0082096 A1 | 4/2010 | Gregorich |
| 2010/0145437 A1 | 6/2010 | Girton et al. |
| 2012/0219696 A1* | 8/2012 | Pacetti ......................... 427/2.25 |

FOREIGN PATENT DOCUMENTS

| | | |
|---|---|---|
| EP | 836839 B1 | 7/2006 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO02/060506 | 8/2002 |
| WO | 02/083039 A1 | 10/2002 |
| WO | WO03/092547 | 11/2003 |
| WO | 2007/021749 A1 | 2/2007 |
| WO | WO2007/021749 | 2/2007 |

OTHER PUBLICATIONS

Basarir et al., "Osseointegration in Arthroplasty: Can Simvastatin Promote one response to Implants?" International Orthopedics (SICOT) (2009) 33:855-859.

Polacco et al. "Biodegradable Hollow Fibres Containing Drug-Loaded Nanoparticles as Controlled Release Systems" Polym International 51:1464-1472 (2002).

PCT Search Report PCT/US2010/039087.

PCT Search Report PCT/US2010/049439.

(56) References Cited

OTHER PUBLICATIONS

PCT Search Report PCT/US2010/049437.
PCT Search Report PCT/US2010/049434.
U.S. Appl. No. 12/428,581, Apr. 23, 2009, Hoff et al.
U.S. Appl. No. 12/500,359, Jul. 9, 2009, Storment et al.
Derle et al., "Particle Engineering Techniques to Enhance Dissolution of Poorly Water Soluble Drugs" International Journal of Current Pharmaceutical Research, vol. 2, Issue 1, 2010, pp. 10-15.
Purvis et al., "Cryogenic Liquids, Nanoparticles, and Microencapsulation" International Journal of Pharmaceutics, 2006.
"Breakthrough Solubilization Technology Targets Stubborn Drug Candidates" Dowpharma.
"Supercritical Carbon-Dioxide Cleaning Defined" Supercritical Carbon-Dioxide Cleaning Technology Review, Jul. 1996.
Berger "Coating Drug-Eluting Arterial Stents Using Ultrasonic Spray Nozzle" ILASS Americas, 19th Annual Conference on Liquid Atomization and Spray Systems, May 2006.

* cited by examiner

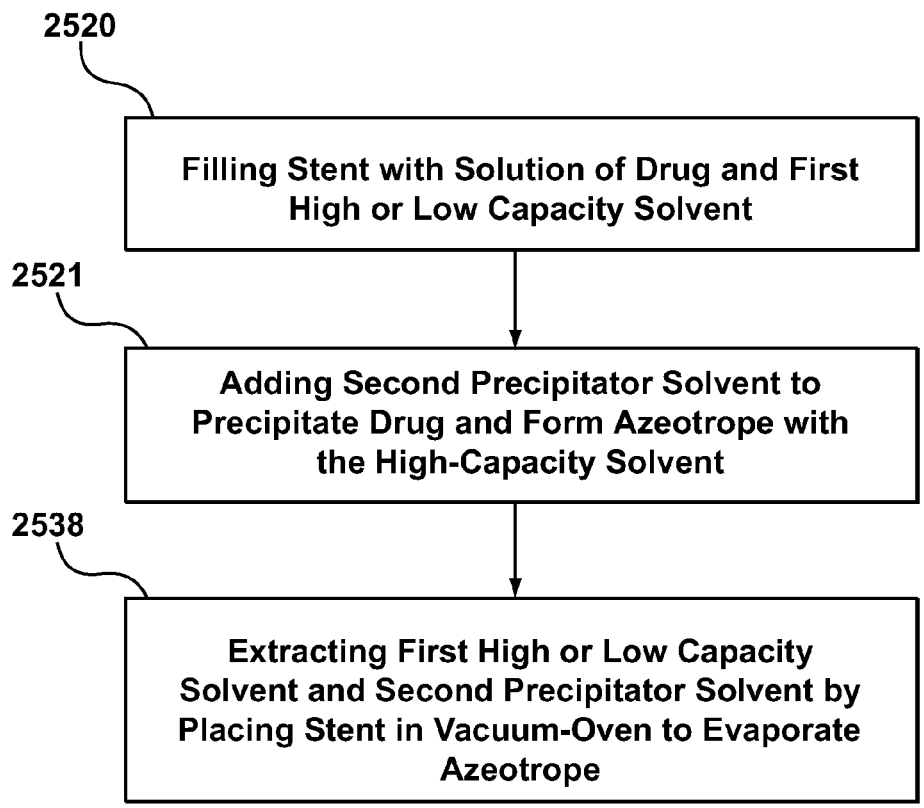
FIG. 25
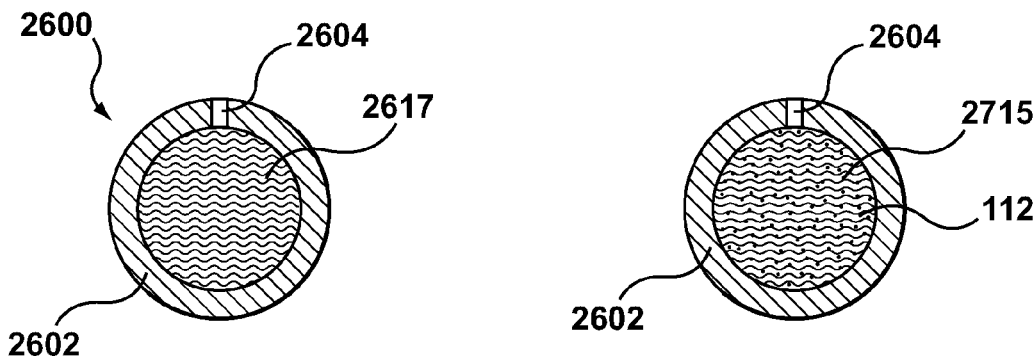
FIG. 26  FIG. 27
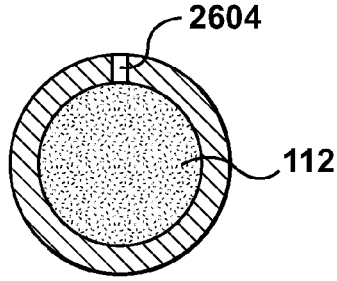
FIG. 28

APPARATUS AND METHODS FOR LOADING A DRUG ELUTING MEDICAL DEVICE

CROSS REFERENCE TO RELATED APPLICATION

This application claims benefit under 35 U.S.C. §119(e) to U.S. Provisional Patent Application No. 61/244,050, filed Sep. 20, 2009.

FIELD OF THE INVENTION

Embodiments hereof relate to tubular implantable medical devices that release a therapeutic substance, and apparatuses and methods of filling such medical devices with the therapeutic substance.

BACKGROUND OF THE INVENTION

Drug-eluting implantable medical devices have become popular in recent times for their ability to perform their primary function such as structural support and their ability to medically treat the area in which they are implanted. For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include sirolimus and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a drug or a combination of drugs. Once the medical device is implanted at a target location, the drug(s) is released from the polymer for treatment of the local tissues. The drug(s) is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical device. Controlling the rate of elution using polymer coatings is also difficult.

Accordingly, drug-eluting medical devices that enable increased quantities of a drug to be delivered by the medical device, and allow for improved control of the elution rate of the drug, and improved methods of forming such medical devices are needed. Co-pending U.S. application Ser. No. 12/500,359, filed Jul. 9, 2009, U.S. Provisional Application No. 61/244,049, filed Sep. 20, 2009, U.S. Provisional Application No. 61/244,050, filed Sep. 20, 2009, and co-pending U.S. application Ser. No. 12/884,343, each incorporated by reference herein in their entirety, disclose methods for forming drug-eluting stents with hollow struts. In some applications, such as coronary stents, the diameter of the hollow strut lumen to be filled with the drug or therapeutic substance is extremely small, e.g. about 0.0015 in., which may make filling the lumen difficult. As such apparatus for and methods of loading a drug within a lumen of a hollow strut of a stent are needed.

BRIEF SUMMARY OF THE INVENTION

Embodiments hereof are directed to methods and apparatus for loading a therapeutic substance or drug within a lumenal space of a hollow wire having a plurality of side openings along a length thereof that forms a drug-eluting hollow stent with a plurality of side drug delivery openings. Loading a drug within the lumenal space of the hollow stent includes a drug filling step in which the drug is mixed with a solvent or dispersion medium in order to flow within the lumenal space of the hollow wire. The lumenal space may be filled with the drug solution or suspension in a reverse fill process through drug delivery openings of the hollow stent and/or may be filled with the drug solution or suspension in a forward fill process through open ends of the hollow stent. After the lumenal space is filled with the drug solution or suspension, a solvent or dispersion medium extracting step is performed to extract the solvent or dispersion medium from within the lumenal space such that primarily only the drug or the drug plus one or more excipients remain within the hollow stent. A stent cleaning step may be performed to an exterior surface of the hollow stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 7A illustrates a hexane based dispersant that has been homogenized to nano-sized drug particles, while FIG. 7B illustrates a hexane based dispersant system that has not been homogenized.

FIG. 25 is a flowchart of a method for precipitating a drug within the hollow wire of a drug eluting stent, wherein the method utilizes the formation of an azeotrope.

FIGS. 26, 27, and 28 are cross-sectional views illustrating the method of FIG. 25 to show the formation of the azeotrope within the hollow wire of the drug eluting stent.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Drug eluting stents described herein may be utilized in the context of treatment of blood vessels such as the coronary, carotid and renal arteries, or any other body passageways where it is deemed useful. More particularly, drug eluting stents loaded with a therapeutic substance by methods described herein are adapted for deployment at various treatment sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents. Furthermore, there is no intention to be bound by any expressed or implied theory presented in the preceding technical field, background, brief summary or the following detailed description.

Hollow Wire Drug-Eluting Stent

Figure 1:
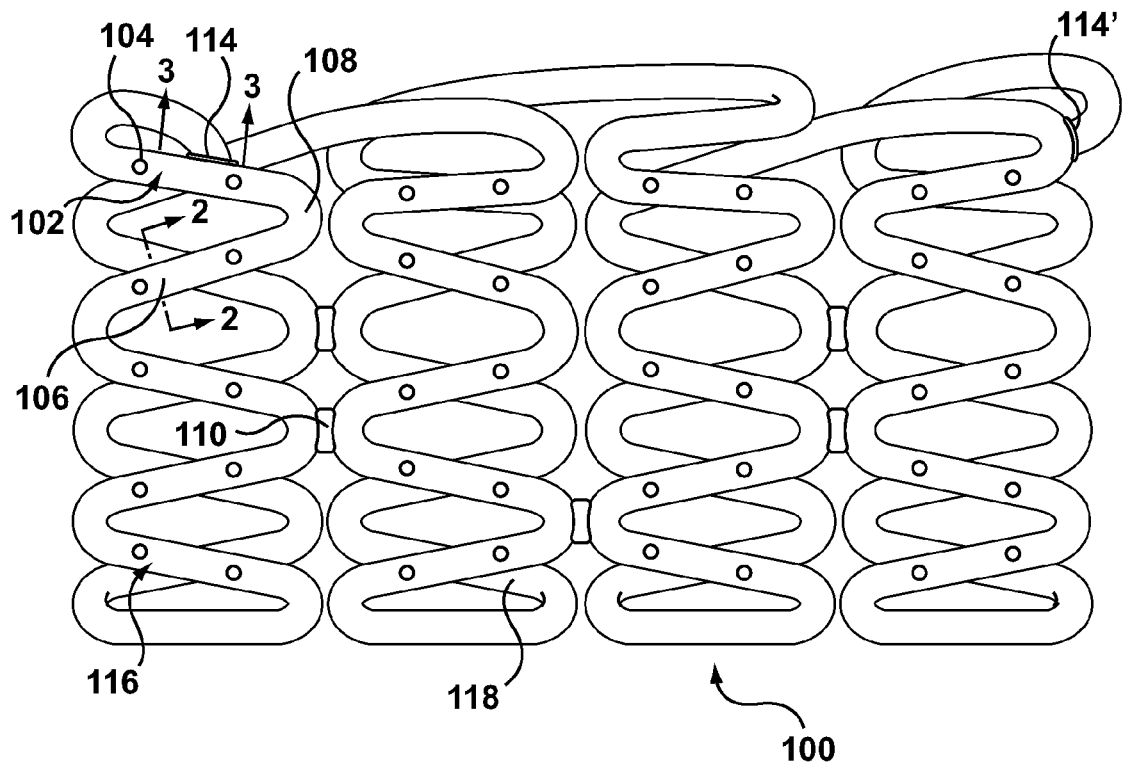
FIG. 1 is a side view of a drug eluting stent formed from a hollow wire according to one embodiment hereof.
Figure 2:
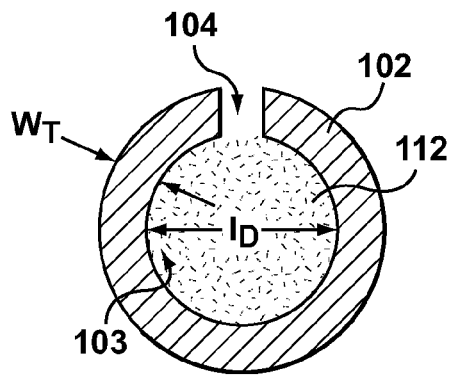
FIG. 2 is a cross-sectional view taken along line 2-2 of FIG. 1.
Figure 3:
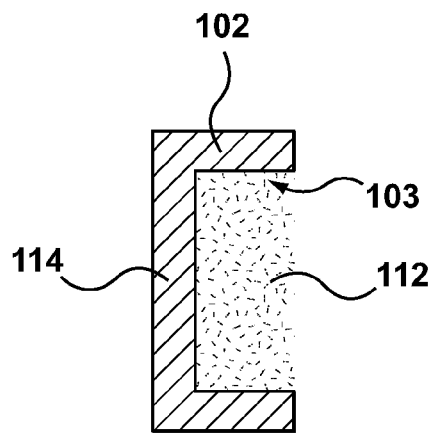
FIG. 3 is a sectional view taken along line 3-3 at an end of the hollow wire of FIG.

An embodiment of a stent 100 to be loaded with a drug in accordance with embodiments hereof is shown in FIGS. 1-3. In particular, stent 100 is formed from a hollow wire 102 and hereinafter may be referred to as a hollow stent or a hollow core stent. Hollow wire 102 defines a lumen or luminal space 103, which may be formed before or after being shaped into a desired stent pattern. In other words, as used herein, "a stent formed from a hollow wire" includes a straight hollow wire shaped into a desired stent pattern, a solid wire having a core that is at least partially removed after the solid wire is shaped into a desired stent pattern to have a discontinuous lumen or luminal space therethrough, or a stent constructed from any suitable manufacturing method that results in a tubular component formed into a desired stent pattern, the tubular component having a lumen or luminal space extending continuously or discontinuously therethrough. As shown in FIG. 1, hollow wire 102 is formed into a series of generally sinusoidal waves including generally straight segments 106 joined by bent segments or crowns 108 to form generally tubular stent 100 that defines a central blood flow passageway or lumen therethrough. Selected crowns 108 of longitudinally adjacent sinusoids may be joined by, for example, welds 110 as shown in FIG. 1. Methods of loading a drug within a hollow stent in accordance with embodiments hereof are not limited to hollow stents having the pattern shown in FIG. 1. Hollow stents formed into any pattern suitable for use as a stent may be loaded with a drug by the methods disclosed herein. For example, and not by way of limitation, hollow stents formed into patterns disclosed in U.S. Pat. No. 4,800,082 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety, may be loaded with a drug by the methods disclosed herein.

As shown in FIG. 2, hollow wire 102 of stent 100 allows for a therapeutic substance or drug 112 to be deposited within lumen or luminal space 103 of hollow wire 102. Lumen 103 may continuously extend from a first end 114 to a second end 114' of hollow wire 102 or may be discontinuous such as being only within straight segments 106 and not within crowns 108 or may be discontinuous such as being within the straight segments 106 and a portion of the crowns 108. Although hollow wire 102 is shown as generally having a circular cross-section, hollow wire 102 may be generally elliptical or rectangular in cross-section. Hollow wire 102 may have a wall thickness $W_T$ in the range of 0.0004 to 0.005 inch with an inner or lumen diameter $I_D$ ranging from 0.0005 to 0.02 inch. Hollow wire 102 that forms stent 100 may be made from a metallic material for providing artificial radial support to the wall tissue, including but not limited to stainless steel, nickel-titanium (nitinol), nickel-cobalt alloy such as MP35N, cobalt-chromium, tantalum, titanium, platinum, gold, silver, palladium, iridium, and the like. Alternatively, hollow wire 102 may be made from a hypotube, which as is known in the art is a hollow metal tube of very small diameter of the type typically used in manufacturing hypodermic needles. Alternatively, hollow wire 102 may be formed from a non-metallic material, such as a polymeric material. The polymeric material may be biodegradable or bioresorbable such that stent 100 is absorbed in the body after being utilized to restore patency to the lumen and/or provide drug delivery.

Hollow wire 102 further includes drug-delivery side openings or ports 104 dispersed along its length to permit therapeutic substance or drug 112 to be released from lumen 103. Side openings 104 may be disposed only on generally straight segments 106 of stent 100, only on crowns 108 of stent 100, or on both generally straight segments 106 and crowns 108. Side openings 104 may be sized and shaped as desired to control the elution rate of drug 112 from hollow stent 100. More particularly, side openings 104 may be slits or may be holes having any suitable cross-section including but not limited to circular, oval, rectangular, or any polygonal cross-section. Larger sized side openings 104 generally permit a faster elution rate and smaller sized side openings 104 generally provide a slower elution rate. Further, the size and/or quantity of side openings 104 may be varied along hollow stent 100 in order to vary the quantity and/or rate of drug 112 being eluted from stent 100 at different portions of hollow stent 100. Side openings 104 may be, for example and not by way of limitation, 5-30 μm in width or diameter. Side openings 104 may be provided only on an outwardly facing or abluminal surface 116 of hollow stent 100, as shown in FIG. 2, only on the inwardly facing or lumenal surface 118 of hollow stent 100, on both surfaces, or may be provided anywhere along the circumference of wire 102.

In various embodiments hereof, a wide range of therapeutic agents may be utilized as the elutable therapeutic substance or drug 112 contained in lumen 103 of hollow wire 102, with the pharmaceutically effective amount being readily determined by one of ordinary skill in the art and ultimately depending, for example, upon the condition to be treated, the nature of the therapeutic agent itself, the tissue into which the dosage form is introduced, and so forth. Further, it will be understood by one of ordinary skill in the art that one or more therapeutic substances or drugs may be loaded into hollow wire 102. Drug 112 delivered to the area of a stenotic lesion can be of the type that dissolves plaque material forming the stenosis or can be an anti-platelet formation drug, an anti-thrombotic drug, or an anti-proliferative drug. Such drugs can include TPA, heparin, urokinase, or sirolimus, for example. Of course stent 100 can be used for delivering any suitable medications to the walls and interior of a body vessel including one or more of the following: anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In accordance with embodiments hereof, hollow stent 100 is loaded or filled with therapeutic substance or drug 112 prior to implantation into the body. Open ends 114, 114' of wire 102 may be closed or sealed either before or after the drug is loaded within fluid passageway 103 as shown in the sectional view of FIG. 3, which is taken along line 3-3 of FIG. 1. Once positioned inside of the body at the desired location, hollow stent 100 is deployed for permanent or temporary implantation in the body lumen such that therapeutic substance 112 may elute from lumen 103 via side openings 104.

Figure 4:
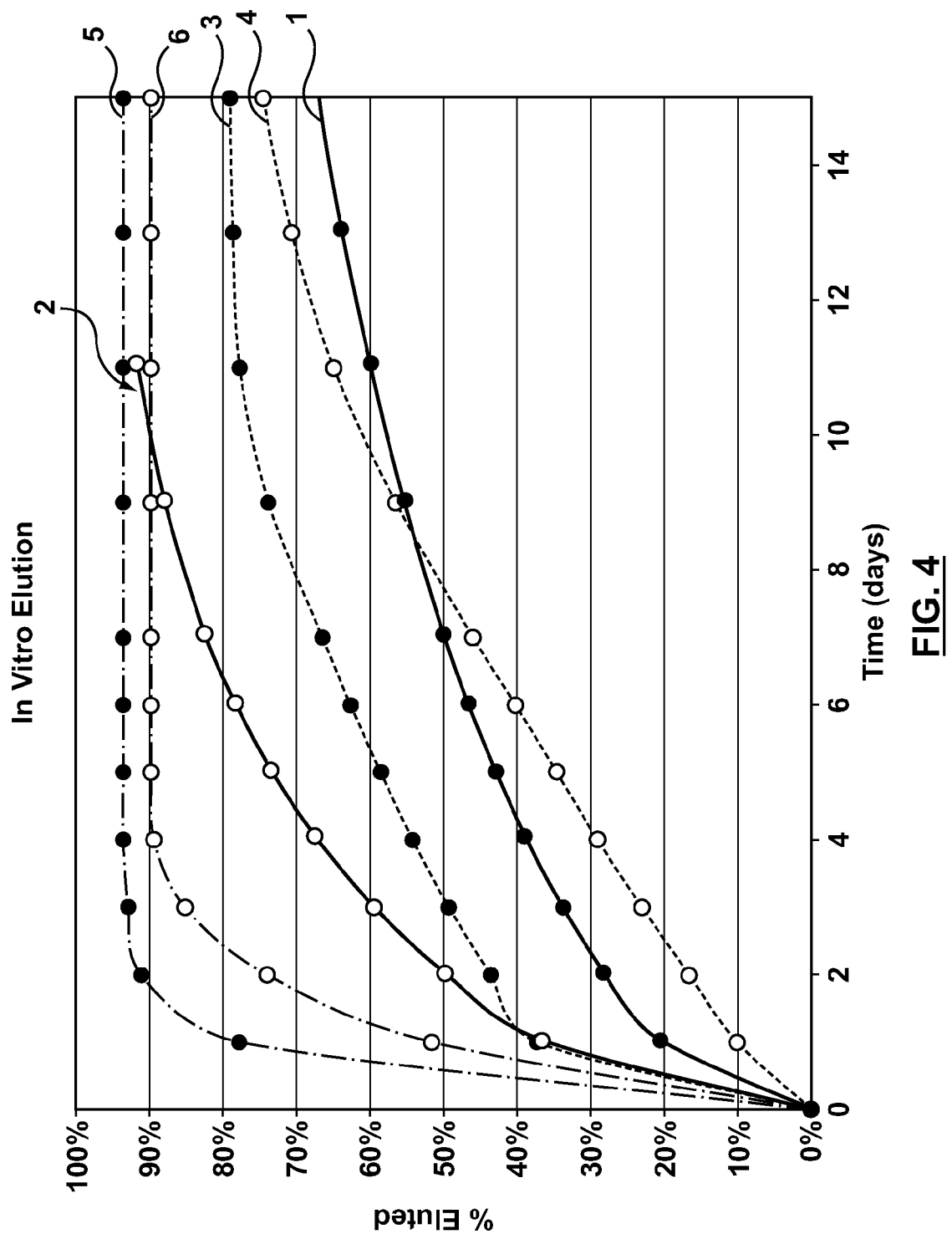
FIG. 4 is a chart of elution rates for a hollow drug-eluting stent.

FIG. 4 shows a chart of elution rates for a drug-eluting hollow stent. The chart shows the percentage of therapeutic substance eluted as a function of time. The lines marked 1 and 2 represent a commercially available drug eluting stent with the therapeutic substance disposed in a polymer on the surface of the stent that has produced desirable clinical efficacy data. The lines marked 3, 4, 5, and 6 are tests using a hollow stent with the lumen filled with therapeutic substance according to methods described herein, with no polymer on the surface of the stent. In particular, the lumen of the hollow stent for the lines marked 3, 4, 5, and 6 were filled using the azeotrope fill process followed by vacuum drying for solvent extraction and stent cleaning via a histobrush as described in more detail herein. The lines marked 3 and 4 are tests using a hollow stent with one 6 μm hole on each strut and lines marked 5 and 6 are tests using a hollow stent with three 10 μm holes on each strut. In particular, the hollow stents used in tests marked with lines 3 and 5 were filled with a solution of sirolimus and tetrahydrofuran followed by an addition of hexane to precipitate the sirolimus and then the solvent was extracted from the hollow stent lumens and the exterior of the stent cleaned. The hollow stents used in tests marked with lines 4 and 6 were filled with a solution of sirolimus, tetrahydrofuran and an excipient followed by an addition of hexane to precipitate the sirolimus and then the solvent and the non-solvent were extracted from the hollow stent lumens and the exterior of the stent cleaned. The chart of elution rates shows that controlled release may be achieved via a hollow stent filled with therapeutic substance and a hollow stent filled with therapeutic substance plus an excipient, and that the hollow filled stent can achieve similar elution curves as drug eluting stent with the therapeutic substance disposed in a polymer on the surface of the stent. Hollow filled stent achieving similar elution curves as drug-polymer coated stent are expected to have similar clinical efficacy while simultaneously being safer without the polymer coating. In addition, the chart of elution rates show that a variety of elution curves can be achieved from hollow stent filled with therapeutic substance or a hollow stent filled with therapeutic substance plus an excipient.

Overview of Stent Filling Process

Figure 5:
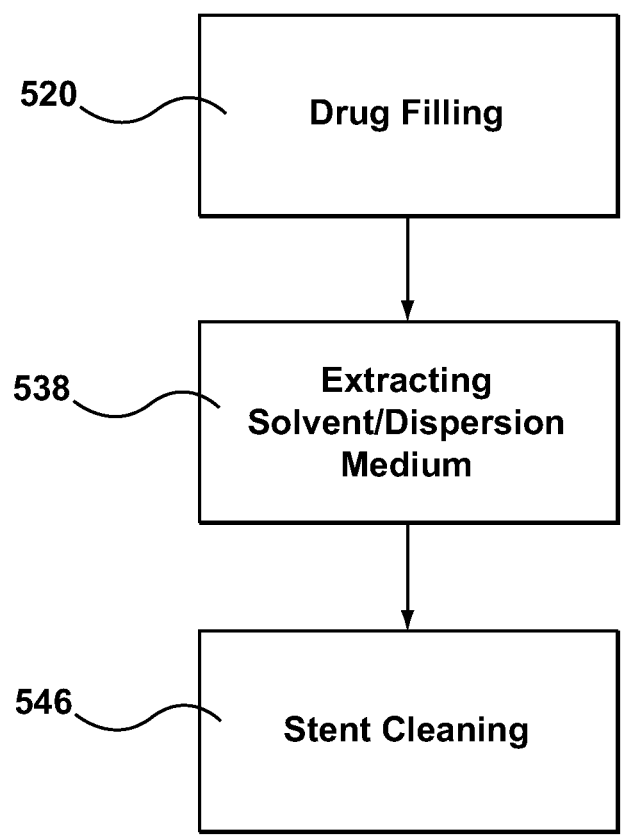
FIG. 5 is a flowchart illustrating three main steps of a process for loading a drug or therapeutic substance into a hollow wire of the stent of FIG. 1.

A general method of loading a drug within lumen 103 of hollow stent 100 in accordance with embodiments hereof is depicted in FIG. 5 to include the steps of drug filling 520, solvent extracting 538, and stent cleaning 546. More particularly in a drug filling step 520, therapeutic substance 112 is generally mixed with a solvent or dispersion medium/dispersant in order to be loaded into lumen 103 of hollow wire 102. In addition, the therapeutic substance 112 can be mixed with an excipient to assist with elution in addition to the solvent or dispersion medium/dispersant in order to be loaded into lumen 103 of hollow wire 102. Hereinafter, the term "drug formulation" may be used to refer generally to a therapeutic substance, a solvent or dispersion medium, and any excipients/additives/modifiers added thereto. After lumen 103 of hollow stent 100 is filled with the drug formulation, a solvent/dispersion medium extracting step 538 is performed to extract the solvent or dispersion medium from within the lumenal space such that primarily only therapeutic substance 112 or therapeutic agent 112 and one or more excipients remain within hollow stent 100 to be eluted into the body. Lastly, a stent cleaning step 546 is performed to hollow stent 100 such that the outside surface of hollow stent 100 will be substantially free of therapeutic agent 112 except where side openings 104 are present. Depending on the apparatus and methods used in accordance herewith, one or more of the steps of drug filling, solvent/dispersion medium extracting and/or stent cleaning may be performed on hollow wire 102 before or after hollow wire 102 is formed into stent 100. For example, some of the processes described below require that hollow wire 102 be straight in order to load therapeutic substance within the luminal space, while other processes described below may be utilized to fill hollow wire 102 after wire 102 is formed in the desired sinusoidal, helical, or other stent configuration.

Drug Filling Step

Figure 5A:
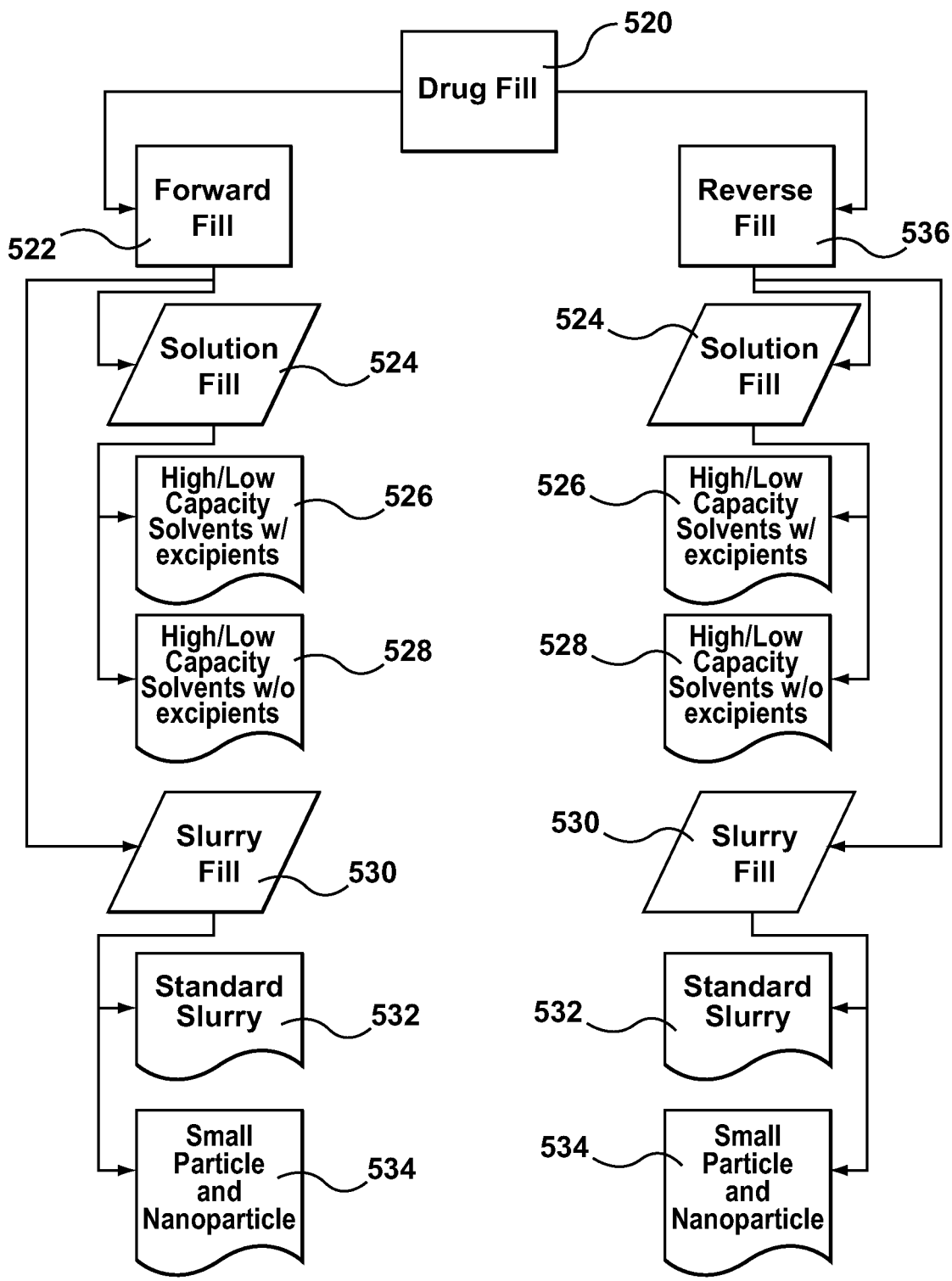
FIG. 5A is a more detailed flowchart of a drug filling step of FIG. 5.

FIG. 5A illustrates a more detailed flowchart of drug filling step 520. More particularly in accordance with embodiments hereof, a drug formulation may be loaded into hollow wire 102 via either a forward fill method 522 or a reverse fill method 536. Forward fill methods include filling hollow wire 102 through one or both of open ends 114, 114' thereof while the drug delivery openings 104 are generally blocked or plugged in some manner to prevent leakage therethrough. Reverse fill methods include filling hollow wire 102 through the plurality of side openings 104. In some reverse fill methods, hollow wire 102 is also filled via one or both of open ends 114, 114' thereof in addition to through side openings 104. Thus, reverse fill methods leverage the drug delivery ports 104 as access points to fill the lumenal space of hollow stent 100. By utilizing multiple access points spaced along the length of hollow wire 102, the drug formulation may be more evenly introduced into lumen 103 such that the entire length of lumen 103 may be filled with the drug formulation. In addition, if a partial blockage of lumen 103 or side openings 104 occurs during a reverse fill process, filling of the remainder of lumen 103 is not seriously affected since the filling may continue via the remaining side openings 104 as the filling of the luminal space is not dependent upon filling from end to end.

As mentioned above, in some stent configurations lumen 103 is discontinuous along the length of hollow wire 102. For example, as described in copending U.S. patent application Ser. No. 12/884,343, previously incorporated by reference herein, a core of hollow wire 102 is left within the crowns of hollow stent 100 to make hollow stent 100 more radiopaque. Filling a drug formulation in a forward fill manner through lumen 103 of hollow wire 102 from one and/or the other open ends 114, 114' becomes impossible due to the discontinuous nature of the lumen. Thus, filling in a reverse fill manner is particularly advantageous for stents formed from a hollow wire having a discontinuous lumen because the drug formulation laterally fills the separated lumens at the same time through the drug delivery side openings or ports 104.

As shown in FIG. 5A, regardless of whether a forward fill method 522 or a reverse fill method 536 is utilized, therapeutic substance 112 is mixed with a solvent or solvent mixture as a solution 524 or mixed with a dispersion medium as a slurry/suspension 530 before being loaded into hollow wire 102. Solution 524 is a homogeneous mixture in which therapeutic substance 112 dissolves within a solvent or a solvent mixture. In one embodiment, solution 524 includes a high-capacity solvent 528 which is an organic solvent that has a high capacity to dissolve therapeutic substance 112. High capacity as utilized herein is defined as an ability to dissolve therapeutic substance 112 at concentrations greater than 500 mg of substance per milliliter of solvent. Examples of high capacity drug dissolving solvents for sirolimus and similar substances include but are not limited to tetrahydrofuran (THF), di-chloromethane (DCM), chloroform, and di-methyl-sulfoxide (DMSO). In addition to the high-capacity solvent, solution 524 may include an excipient 526 in order to assist in drug elution. In one embodiment, excipient 526 may be a surfactant such as but not limited to sorbitan fatty acid esters such as sorbitan monooleate and sorbitan monolaurate, polysorbates such as polysorbate 20, polysorbate 60, and polysorbate 80, cyclodextrins such as 2-hydroxypropyl-beta-cyclodextrin and 2,6-di-O-methyl-beta-cyclodextrin, sodium dodecyl sulfate, octyl glucoside, and low molecular weight poly(ethylene glycol)s. In another embodiment, excipient 526 may be a hydrophilic agent such as but not limited to salts such as sodium chloride and other materials such as urea, citric acid, and ascorbic acid. In yet another embodiment, excipient 526 may be a stabilizer such as but not limited to butylated hydroxytoluene (BHT). Depending on the desired drug load, a low capacity solvent can also be chosen for its reduced solubility of therapeutic substance 112. Low capacity is defined as an ability to dissolve therapeutic substance 112 at concentrations typically below 500 mg of drug per milliliter solvent. Examples of low capacity drug dissolving solvents for sirolimus and similar substances include but are not limited to methanol, ethanol, propanol, acetonitrile, ethyl lactate, acetone, and solvent mixtures like tetrahydrafuran/water (9:1 weight ratio). After solution 524 is loaded into hollow stent 100, therapeutic substance 112 may be precipitated out of the solution, e.g., transformed into solid phase, and the majority of the residual solvent and any nonsolvent, if present, may be extracted from the lumenal space of hollow wire 102 such that primarily only therapeutic substance 112 or therapeutic substance 112 and one or more excipients 526 remain to be eluted into the body.

In slurry/suspension form 530, therapeutic substance 112 is not dissolved but rather dispersed as solid particulate in a dispersion medium, which refers to a continuous medium in liquid form within which the solid particles are dispersed. Using a suspension eliminates the need to precipitate out therapeutic substance 112 from the solvent as is the case with a solution, because therapeutic substance 112 remains a solid in the dispersion medium when mixed together. Examples of dispersion mediums with an inability to dissolve therapeutic substance 112 depend on the properties of therapeutic substance 112. For example, suitable dispersion mediums with an inability to dissolve sirolimus include but are not limited to water, hexane, and other simple alkanes, e.g., C5 thru C10. Certain excipients, suspending agents, surfactants, and/or other additives/modifiers can be added to the drug slurry/suspension to aid in suspension and stabilization, ensure an even dispersion of drug throughout the suspension and/or increase the surface lubricity of the drug particles. Surfactants thus generally prevent therapeutic substance 112 from floating on the top of or sinking to the bottom of the dispersion medium. Examples of surfactants include but are not limited to sorbitan fatty acid esters such as sorbitan monooleate and sorbitan monolaurate, polysorbates such as polysorbate 20, polysorbate 60, and polysorbate 80, and cyclodextrins such as 2-hydroxypropyl-beta-cyclodextrin and 2,6-di-O-methyl-beta-cyclodextrin. In one embodiment, the targeted amount of therapeutic substance 112 is suspended in the dispersion medium and the appropriate additive/modifier is added on a 0.001 to 10 wt % basis of total formulation. In addition, an excipient such as urea or 2,6-di-Omethyl-beta-cylcodextrin may be added to slurry/suspension 530 in order to assist in drug elution.

One advantage of utilizing slurry/suspension 530 as opposed to solution 524 is that since therapeutic substance 112 is already in solid form within the dispersion medium, openings 104 will not become blocked with dried drug solution. More particularly, when filling hollow stent 100 with solution 524, a fraction of solution 524 within lumen 103 may escape or leak through openings 104 onto the outer surface of hollow stent 100. The leaking occurs due to surface tension/capillary action or outflow from the transferring process. Solution 524 on the outer surface of the stent will dry quicker than solution 524 contained within lumen 103 of hollow wire 102. The net effect is a cast layer of drug that may occlude side openings 104, thereby making further solvent extraction difficult. The residual solvent trapped within the lumenal space can have a detrimental effect on biocompatibility as well as cause complications in predicting the effective drug load. By utilizing slurry/suspension 530 rather than solution 524, the drug and dispersion medium remain separated and a cast layer of drug does not form.

The particle size of therapeutic substance 112 when suspended in slurry/suspension 530 influences various factors, including the viscosity of the suspension and the stability of the suspension meaning how long the particles remain suspended before settling. In one embodiment labeled standard slurry/suspension 532, drug particle diameters ranging from 1 micron to 50 microns can be utilized. Therapeutic substance 112 may be pelletized prior to filling the lumen of the hollow wire. The control of particle size distribution or pelletizing of the drug can occur through various paths including mechanical means such as grinding processes and non-mechanical means such as precipitation processes. When a forward filling method is being utilized, the pellets are smaller than the lumenal space of the stent such that the drug particles can pass through the ends thereof. When a reverse filling method is being utilized, the pellets are smaller than the openings 104 in the stent such that the drug particles can pass therethrough. The pelletized drug in slurry/suspension 532 may be loaded into the lumen of the stent by vibration/sonication, pressure filling, or any other suitable technique described herein. Pelletizing the therapeutic substance provides substantially uniform size of the particles for improved consistency in dosing and easier loading.

In another embodiment labeled small particle and nanoparticle slurry/suspension 534, drug particle diameters ranging from 1 nanometer to 1000 nanometers can be utilized. Particles in the less than 100 nanometer size range are commonly referred to as nanoparticles. Small particle size drug and in particular nanoparticles are an attractive candidate for use in drug delivery as the smaller particles allow for more efficient loading of drug into the stent. More particularly, the drug particles are significantly smaller than the lumenal space 103 and side openings 104. Thus in a forward fill method, the small particles of drug can easily transport into lumen 103 of hollow wire 102 via the open ends 114, 114' of the stent. In a reverse fill method, the drug can easily traverse side openings 104 to fill lumen 103 of hollow wire 102.

In addition to the aforementioned efficiencies, small particle and nanoparticle drug has advantages in drug delivery. Specifically, as the particle size is reduced, the solubility of the drug is increased in situ. This benefit becomes more apparent when the particle size is reduced from micron sized particles to nanometer diameter particles. Particles in the nanometer range also have the ability to diffuse as whole particles from the stent to the tissue by using the concentration gradient that exists between the drug source and the target tissue. As a result, the rate of transport from the lumen of stent 100 to the tissue is increased.

Figure 6:
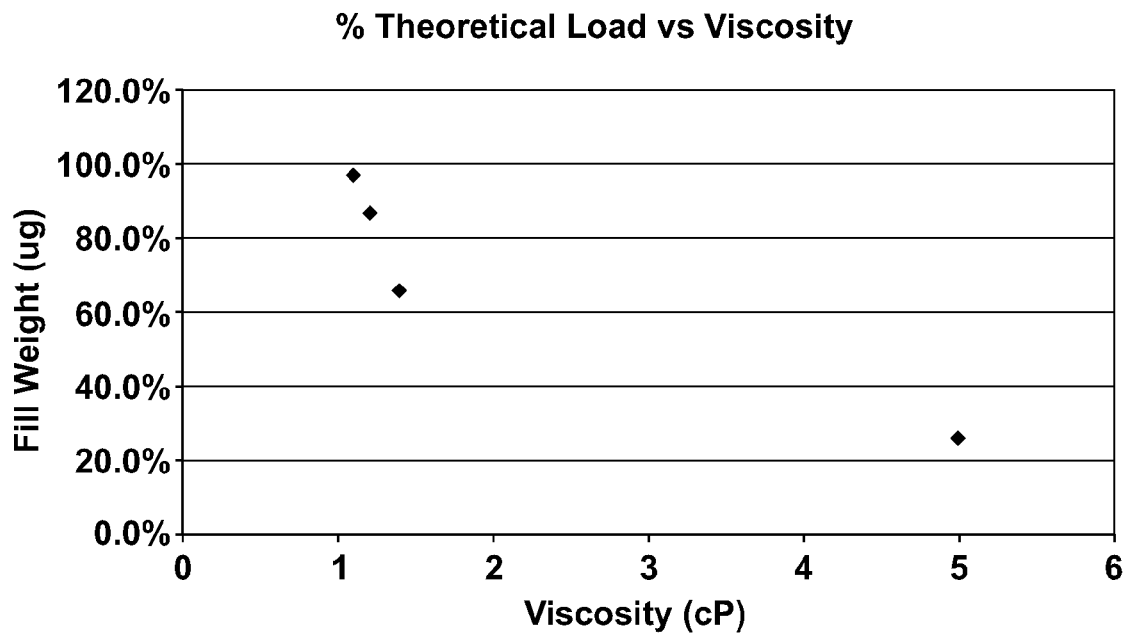
FIG. 6 is a chart illustrating the effect of viscosity on drug loading.
Figures 7A, 7B:
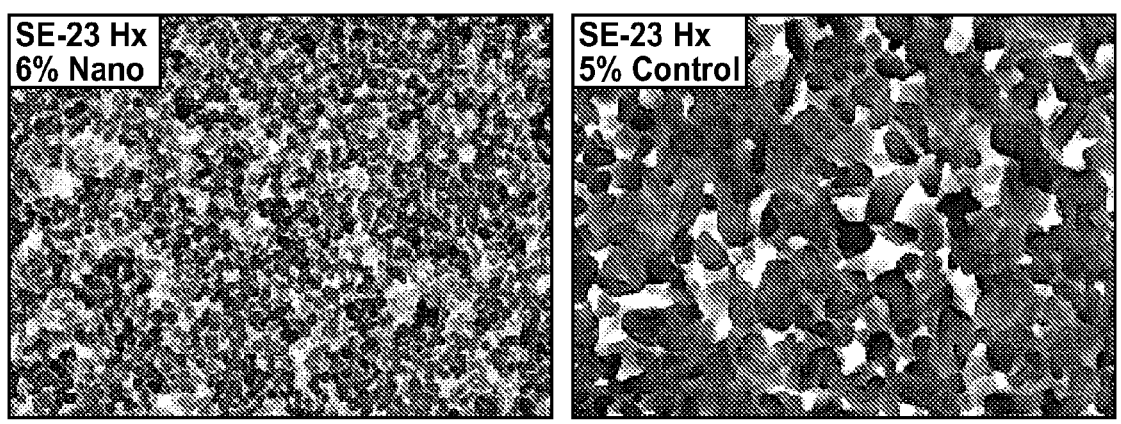

Small particle and nanoparticle drug may be created by any suitable method, including but not limited to homogenization/microfluidics, precipitation, supercritical $CO_2$, ball milling, and rod milling. When creating a slurry/suspension having nanoparticles, it is important that the viscosity of the slurry/suspension is sufficiently low to allow transport across openings 104 and into the stent. FIG. 6 is a chart that illustrates how drug loading is affected when particle size is fixed well below the size of side openings 104 and viscosity is altered. In this example, the size of the side openings 104 is 6 um, the particle size is 300 nm and percent fill weight is defined as the ratio of the amount of drug filled in the stent to the theoretical maximum amount. In one embodiment, small particle and nanoparticle drug may be generated via a multiple-pass homogenization process using a surfactant-stabilized dispersant, such as hexane or water. For example, a hexane-based dispersant may be created by mixing hexane with 1% v/v SPAN® 80 and an aqueous-based dispersant may be created by mixing water with 1% v/v Tween® 80. Therapeutic substance 112 is added to create a slurry/suspension that is 10% v/v. The mixture may be sonicated for a predetermined time, e.g. 1-60 minutes, to mix the components before homogenization. A microfluidics homogenizer or microfluidizer is then utilized for homogenization, with settings of 28000 psi and 860 passes. FIG. 7A illustrates a hexane based dispersant (5% v/v) that has been homogenized to nano-sized drug particles, while FIG. 7B illustrates a hexane based dispersant system (5% v/v) that has not been homogenized. After homogenization, dynamic Light Scattering (DLS) and/or SEM may be used to measure particle distributions to ensure that the particles are homogenous. The slurry/suspension may then be diluted to the desired slurry/suspension volume fraction (v/v), and loaded into the lumen of the stent by vibration/sonication, pressure filling, or any other suitable technique described herein.

Drug Filling: Forward Fill High Pressure Gas Embodiment

Figures 8, 9:
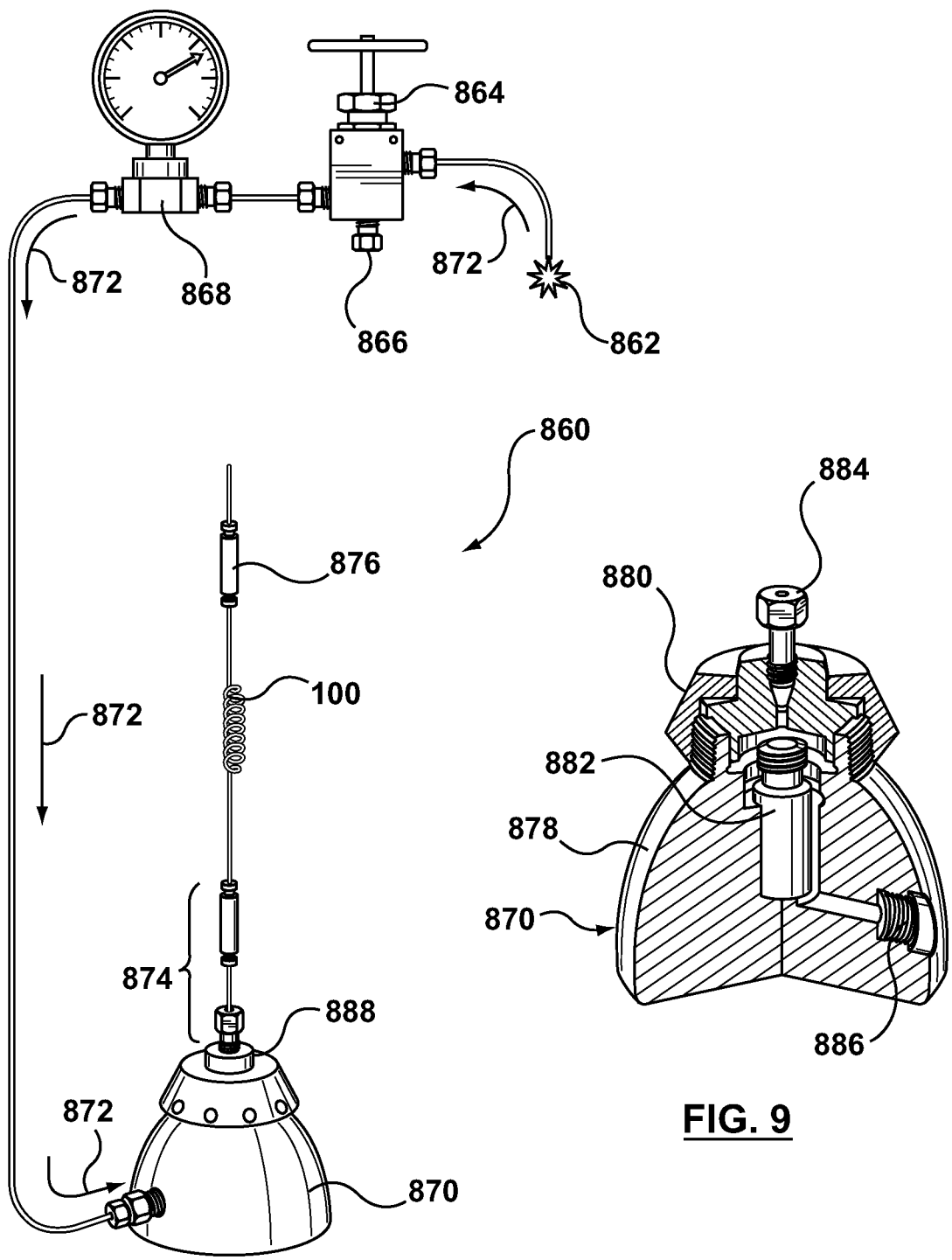
FIGS. 8 and 9 are schematic illustrations of an apparatus for forward filling a drug eluting stent utilizing high-pressure gas.

FIGS. 8 and 9 are schematic illustrations of an apparatus 860 for loading the lumen of a hollow stent in a forward-fill manner with a therapeutic substance in accordance with an embodiment hereof. Apparatus 860 is a high-pressure packing bomb utilized to leverage established capillary column packing techniques, with modifications made for slurry/suspension formulation and/or packing technique(s). More particularly, apparatus 860 includes a pressure source 862, a 3-way valve 864 including a pressure vent 866, a pressure gauge 868, a high-pressure packing unit or bomb 870, and tubing 872 coupling these items together. As shown in FIG. 9, packing unit 870 includes a body 878, a cap lock 880, a vial or container 882 for holding a suspension of a therapeutic substance and a dispersion medium, a side port 886 to which tubing 872 is attached, and a nut 884. Packing unit 870 further includes a cap seal 888, as shown in FIG. 8. Pressurized gas enters packing unit 870 through tubing 872 to pressurize the therapeutic substance suspension held within vial 882. On the exit side of packing unit 870 is a high-pressure fitting 874 for fluidly connecting to a first end of hollow stent 100 such that the lumenal space of hollow wire 102 is in fluid communication with vial 882 to receive the therapeutic substance suspension therefrom. An end fitting 876 including a frit disposed therein is attached to a second end of hollow stent 100 to prevent the therapeutic substance from passing out of hollow stent 100. The frit pore size can range from 0.2 microns to 20 microns depending on the therapeutic substance slurry/suspension density and the therapeutic substance particle size. The aforementioned parts of apparatus 860, except for hollow stent 100, are available from Western Fluids Engineering+MFG, LLC in Wildomar, Calif.

In operation, vial 882 is filled with a slurry/suspension including therapeutic substance 112. In one embodiment vial 882 is filled with a slurry/suspension by adding a fixed mass of therapeutic substance 112 to vial 882 followed by a dispersion medium such that the drug per unit volume concentration ranges from 0.5 mg/ml to 50 mg/ml. The first end of hollow stent 100 is connected to high-pressure packing unit 870 using high pressure connection 874. In an embodiment, a micro stir bar (not shown) may be added to vial 882, and after vial 882 is placed inside and sealed within packing unit 870, high-pressure packing unit 870 may be placed on top of a magnetic stir plate. Inert high pressure gas enters packing unit 870 through side port 886 via tubing 872 and forces the slurry/suspension of therapeutic substance 112 from the vial 882 out of nut 884, through high pressure fitting 874, and into the lumenal space of wire 102 that forms hollow stent 100. The pressurized drug slurry/suspension passes through the lumenal space of hollow stent 100 and the solid particles of therapeutic substance 112 are captured by the frit of end fitting 876. More particularly, the size of the pores of the frit are selected to allow the dispersion medium to pass or be forced therethrough, i.e., downstream thereof, while retaining or capturing the solid drug or therapeutic substance 112 behind or upstream of the frit, thereby packing/loading the lumenal space of the hollow stent 100 from the second end to the first end thereof.

Initial packing pressures can range from 100 to 10,000 psig depending on the desired packing rate, the drug concentration within the slurry/suspension, and the ratio between the inner diameter of hollow wire 102 and drug particle size. In one example, a 6 inch length of hollow tubing, with an inside diameter of 0.004" was filled with sirolimus having a median diameter of approximately 5 um in diameter. The sirolimus was suspended in hexane-isopropanol to achieve a mixture of 90:10 hexane:isopropanol v/v. A 0.5 um frit was utilized on end fitting 876. Packing bomb 870 was pressurized to 500 psi and held there for approximately 55 minutes. Thereafter bomb 870 was depressurized to ambient and then repressurized to 600 psi. The pressure was then gradually increased from 600 to 900 psi over the next 20 min, and then further increased to 1500 psi in 100 psi increments over 30 minutes. In excess of 4 inches of the hollowing tubing was filled with Sirolimus. In embodiments hereof, a diameter of particles of the therapeutic substance may be selected from a range of 1 micron to 50 microns. In an embodiment uniform packing of the hollow stent is aided by periodically reducing the packing pressure to at or near ambient, i.e., depressurizing packing unit 870 to at or near ambient, and subsequently increasing the packing pressure, i.e., re-pressurizing packing unit 870 to the packing pressure, such that periodic pulsatile pressure steps or cycles are employed. In another embodiment, uniform packing may be aided by gradually ramping-up or increasing the packing pressure as hollow stent 100 begins to pack from the second end furthest from packing unit 870 toward the first end. In another embodiment, a vacuum may be applied to the system on the low pressure or downstream side of the frit to assist in drawing the slurry/suspension through the lumenal space of hollow wire 102 toward the frit and to assist in forcing/pulling the dispersion medium through the frit.

In one embodiment, drug delivery openings 104 of hollow stent 100 are temporarily blocked or plugged during the forward fill process in order to minimize leakage of the slurry/suspension as the high pressure gas forces the slurry/suspension through the lumenal space of hollow wire 102. In addition, high pressure gas to forward fill a lumenal space of a hollow wire may be utilized to fill a previously formed hollow stent 100 as shown in FIG. 8 or may be utilized to fill a straight hollow wire or tube 102 that is subsequently formed into hollow stent 100.

Drug Filling: Forward Fill Via Centrifugal Force Embodiments

Figure 10:
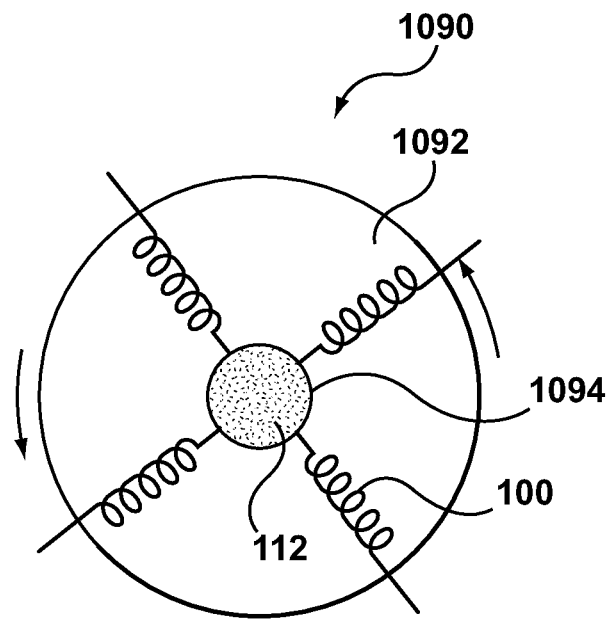
FIGS. 10 and 11 are schematic illustrations of an apparatus for forward filling a drug eluting stent utilizing disc rotation.
Figure 11:
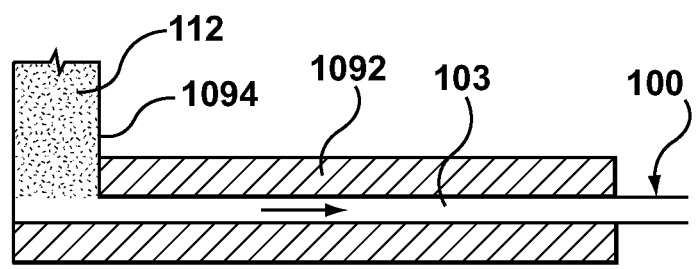

FIGS. 10 and 11 are schematic illustrations of an apparatus 1090 and method for loading the lumen of a hollow stent with a therapeutic substance using centrifugal force in accordance with another embodiment hereof. Apparatus 1090 includes a rotatable disc 1092 and a central filling tube 1094. Filling tube 1094 is filled with a dry therapeutic substance 112. Alternatively, filling tube 1094 is filled with a solution or slurry/suspension containing the therapeutic substance. Central filling tube 1094 is connected to lumen 103 of hollow stent 100. As can be seen, a plurality of hollow stents 100 may be connected to central filling tube 1094. Disc 1092 is rotated at a high speed as indicated by the arrows, thereby forcing therapeutic substance from central filling tube 1094 radially outward into lumens 103 of hollow stents 100.

Figure 12:
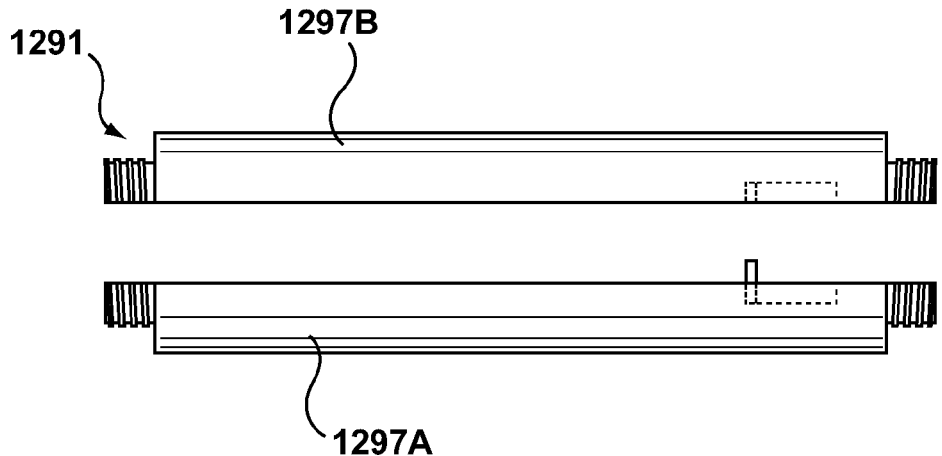
FIGS. 12 and 13 are schematic illustrations of an apparatus for forward filling multiple straight hollow wires utilizing a high G centrifugal force.
Figure 13:
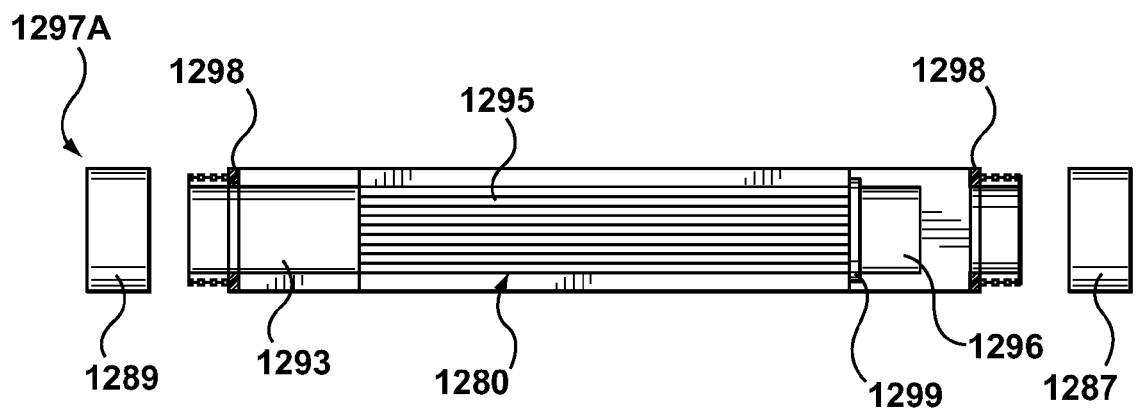

FIGS. 12 and 13 are schematic illustrations of another embodiment utilizing centrifugal force for filling the lumen of multiple hollow stents with a therapeutic substance. A loading apparatus 1291 includes two upper and lower segments 1297A, 1297B, that mate along longitudinally-extending surfaces to form a cylindrical structure. Segments 1297A, 1297B are generally equal halves of the cylindrical loading apparatus 1291 as shown in the side view of FIG. 12. FIG. 13 illustrates a top view of segment 1297A. Loading apparatus 1291 may be formed from polycarbonate, stainless steel, and similar materials and is designed to hold an array or plurality of straight hollow wires 102 that are to be filled with therapeutic substance 112. The straight hollow wires 102 may be placed within a loading compartment 1280 having a plurality of grooves 1295 formed on a flat surface of a respective segment 1297A, 1297B. Grooves 1295 are precisely machined to be of sufficient size and shape to securely accommodate the plurality of straight hollow wires 102 so that the wires are held firmly in position during filling. The bisected design of loading apparatus 1291 facilitates loading of the stents to be filled. Apparatus 1291 includes a wedge-shaped reservoir 1293 for containing a drug slurry/suspension to be loaded within the lumens of the straight hollow wires 102. Loading compartment 1280 is positioned downstream of reservoir 1293 and is in fluid communication with reservoir 1293. Apparatus 1291 further includes a filtering restraining plate 1299 that facilitates the flow of the dispersion medium there-through while permits drug retention upstream thereof. In one embodiment, the filtering restraining plate is an insert of sintered glass that allows fluid flow therethrough while restraining the drug within the lumens of the straight hollow wires 102. A sump chamber 1296 downstream of filtering restraining plate 1299 captures and contains the dispersion medium that flows through apparatus 1291 during the filling procedure, as will be explained in more detail herein. When segments 1297A, 1297B are closed together, rubber gaskets 1298 seal apparatus 1291 such that the slurry/suspension does not leak out of the apparatus during the filling process. Further, a screw cap 1289 having a rubber diaphragm (not shown) and a base ring 1287 tightly hold segments 1297A, 1297B together.

The filling process begins by placing multiple straight hollow wires 102 or tube blanks into grooves 1295 in one half of the loading apparatus 1291. Loading apparatus 1291 is then closed by sandwiching straight hollow wires 102 between segments 1297A, 1297B of apparatus 1291, and base ring 1287 and cap 1289 are screwed into place to seal the unit. Advantageously, to minimize leaking, a compliant rubber coating may be applied to one or more surfaces of loading compartment 1280 such that when loading apparatus 1291 is closed, the rubber coating seals or prevents leaking through drug delivery openings 104 formed within hollow wires 102. Once sealed, reservoir 1293 is filled with a slurry/suspension including a therapeutic substance by injecting the slurry/suspension through the rubber diaphragm of cap 1289. Apparatus 1291 is then placed into a standard centrifuge rotor and a high G centrifugal force is applied across the length of hollow wires 102. The high G centrifugal force drives the drug slurry/suspension into the lumens of the hollow wires 102 and packs the volume with drug particles in a rapid and efficient manner. The speed and time parameters for the centrifuge rotor depend on various factors, including slurry/suspension composition, slurry/suspension viscosity, drug particle size or diameter, friction coefficients, and the degree of desired packing. The centrifugal force acts along the length of the entire hollow tubes 102 and the slurry/suspension moves through hollow wires 102. The dispersion medium of the slurry/suspension passes or flows through filtering restraining plate 1299 and is contained within sump chamber 1296, while the therapeutic substance of the slurry/suspension remains within the lumens of the hollow wires 102. After filling, the straight hollow wires 102 may be formed into the desired stent shape or configuration.

Although described above with respect to a slurry/suspension, apparatus 1291 may also be utilized to fill the lumenal space of hollow wires 102 with a solution of the therapeutic substance. When utilized with a solution, sump chamber 1296 may be omitted and the restraining plate 1299 need not allow passage of liquid therethrough but rather may function to block passage of the solution, thus permitting solution filling within the lumenal space of hollow wires 102. After filling, the lumens of straight hollow wires are filled with the drug solution and the solvent must be subsequently extracted therefrom by any suitable method described herein. In general, filling the hollow wires with a solution requires a shorter duration and a lower speed of the centrifuge rotor.

Figure 14:
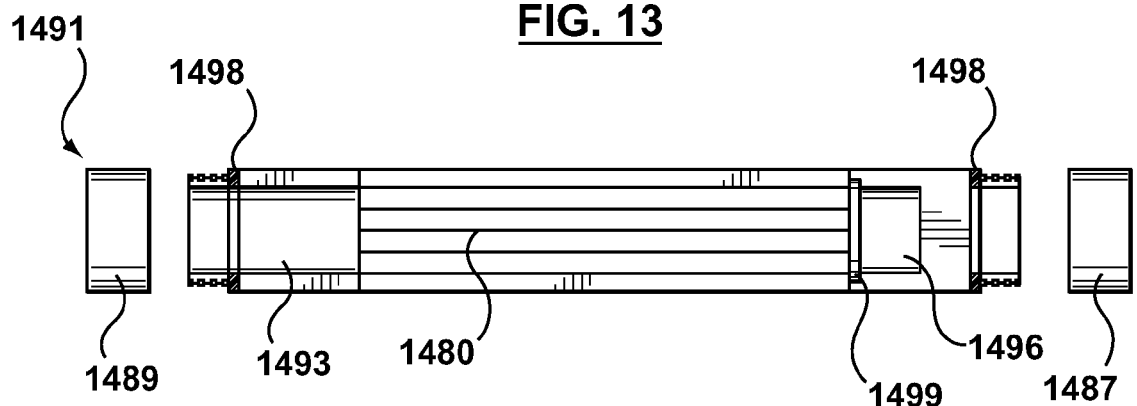
FIG. 14 is a schematic illustration of an apparatus for forward filling a drug eluting stent utilizing a high G centrifugal force.

With reference to FIG. 14, an embodiment for loading a hollow stent via a high G centrifugal force is shown. Similar to loading apparatus 1291, loading apparatus 1491 is generally cylindrical and includes upper and lower longitudinal segments that mate along longitudinally-extending surfaces to form the generally cylindrical structure (not shown). Apparatus 1491 includes a wedge-shaped reservoir 1493 for containing a drug slurry/suspension, a restraining plate or sintered glass insert 1499 that facilitates flow of the dispersion medium therethrough and drug retention upstream thereof, a sump chamber 1496 to capture and contain dispersion medium that flows through apparatus 1491 during the filling procedure, rubber gaskets 1498 to seal apparatus 1491, and a cap 1489 and base ring 1487 to close apparatus 1491. However, rather than having grooves to accommodate straight hollow wires, apparatus 1491 includes a cylindrical loading compartment 1480 formed therein for accommodating a single hollow stent 100. Cylindrical loading compartment 1480 is a particular diameter and length to accommodate the hollow stent. In one embodiment, a rod or core (not shown) may be inserted through the hollow stent during the drug filling process in order to secure or hold the hollow stent firmly in place. The filling process in which a high G centrifugal force is applied across the length of the stent to drive the drug slurry/suspension or solution into the lumenal space of the stent is the same as described above with respect to apparatus 1291.

Figure 15:
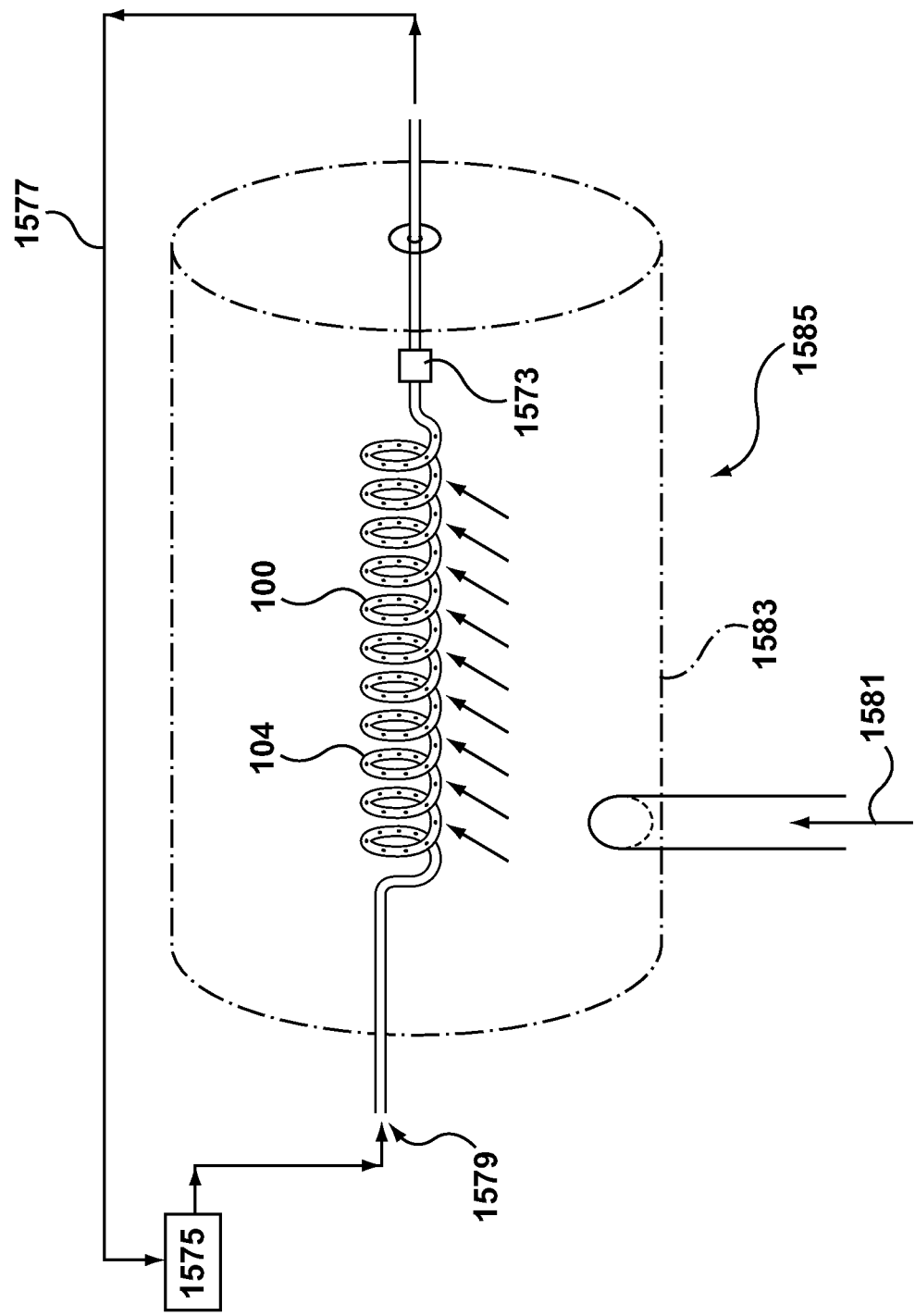
FIG. 15 is a schematic illustration of an apparatus for forward filling a drug eluting stent utilizing supercritical $CO_2$ to precipitate a drug within a drug eluting stent.

Drug Filling: Forward Fill Embodiment Utilizing Supercritical $CO_2$ for Drug Precipitation FIG. 15 is a schematic illustration of an apparatus 1585 and method for loading the lumen of a hollow stent with a therapeutic substance in accordance with another embodiment hereof. Apparatus 1585 includes a pressure chamber 1583 (shown in phantom), a supply 1581 for supercritical carbon dioxide ($SCCO_2$), a supply line 1579 for introducing a solution of a therapeutic substance in a solvent, such as ethanol, and a recirculation system 1577. Supercritical carbon dioxide is carbon dioxide above its critical temperature (31.1° C.) and critical pressure (72.9 atm/7.39 MPa). A hollow stent 100 is disposed in pressure chamber 1583. As the solution is pushed through the lumen of hollow stent 100, supercritical carbon dioxide enters the lumen of hollow stent 100 through openings 104. The supercritical carbon dioxide interacts with the solution to precipitate the therapeutic substance such that the therapeutic substance remains in the lumen of hollow stent 100 and the solvent, such as ethanol, continues to be recirculated through recirculation system 1577. In this embodiment, the properties of $SCCO_2$ are thus utilized as part of the drug filling process in order to precipitate the therapeutic substance out of the solution. A filter 1573 may be located at the exit side of the pressure chamber to capture any of the therapeutic substance that is pushed through hollow stent 100. A therapeutic substance supply 1575 is coupled to the recirculation system 1577 such that the therapeutic substance and solvent are mixed to be introduced as a solution into pressure chamber 1583 through supply line 1579.

In one embodiment, supercritical carbon dioxide to forward fill a stent may be utilized to fill a formed hollow stent 100 as shown in FIG. 15 or may be utilized to fill a straight hollow tube 102 that is subsequently formed into hollow stent 100.

Drug Filling: Forward Fill Syringe Embodiment

Figure 16:
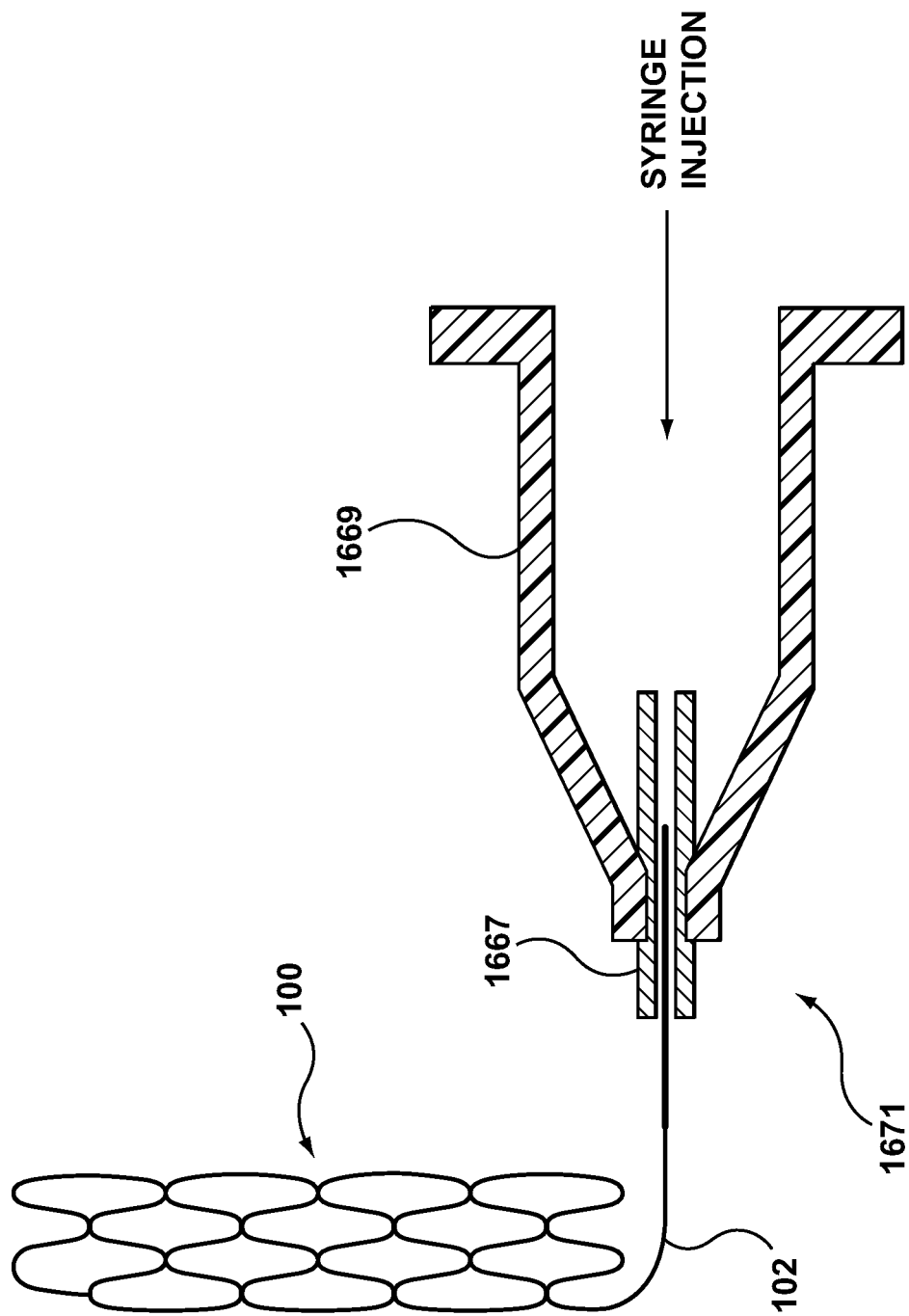
FIG. 16 is a schematic illustration of an apparatus for forward filling a drug eluting stent utilizing a syringe.

FIG. 16 is a schematic illustration of an apparatus 1671 and method for loading the lumen of a hollow stent with a therapeutic substance in accordance with another embodiment hereof. Apparatus 1671 includes a syringe luer connector 1669 and small bore tube coupler 1667 for coupling the syringe luer connector to hollow stent 100. A syringe (not shown) injects a therapeutic substance into the lumen of hollow stent 100 through the syringe luer connector and small bore tube coupler. The therapeutic substance may be mixed with a solvent or dispersion medium to form a solution or slurry/suspension, respectively. Exemplary solvents or dispersion mediums include ethanol, chloroform, acetone, tetrahydrofuran, dimethyl sulfoxide, ethyl lactate, isopropyl alcohol, acetonitrile, water, and others as would be known to one of ordinary skill in the art and/or described herein. In one embodiment, drug delivery openings 104 of hollow stent 100 are blocked or plugged during the forward fill process in order to minimize leakage as the syringe injects the therapeutic substance and solvent/dispersion medium through the lumen of the stent. In addition, a syringe to forward fill a stent may be utilized to fill a hollow stent 100 as shown in FIG. 16 or may be utilized to fill a straight hollow tube 102 that is subsequently formed into hollow stent 100.

Drug Filling: Forward Fill Embodiment Utilizing Vibration

Figure 17:
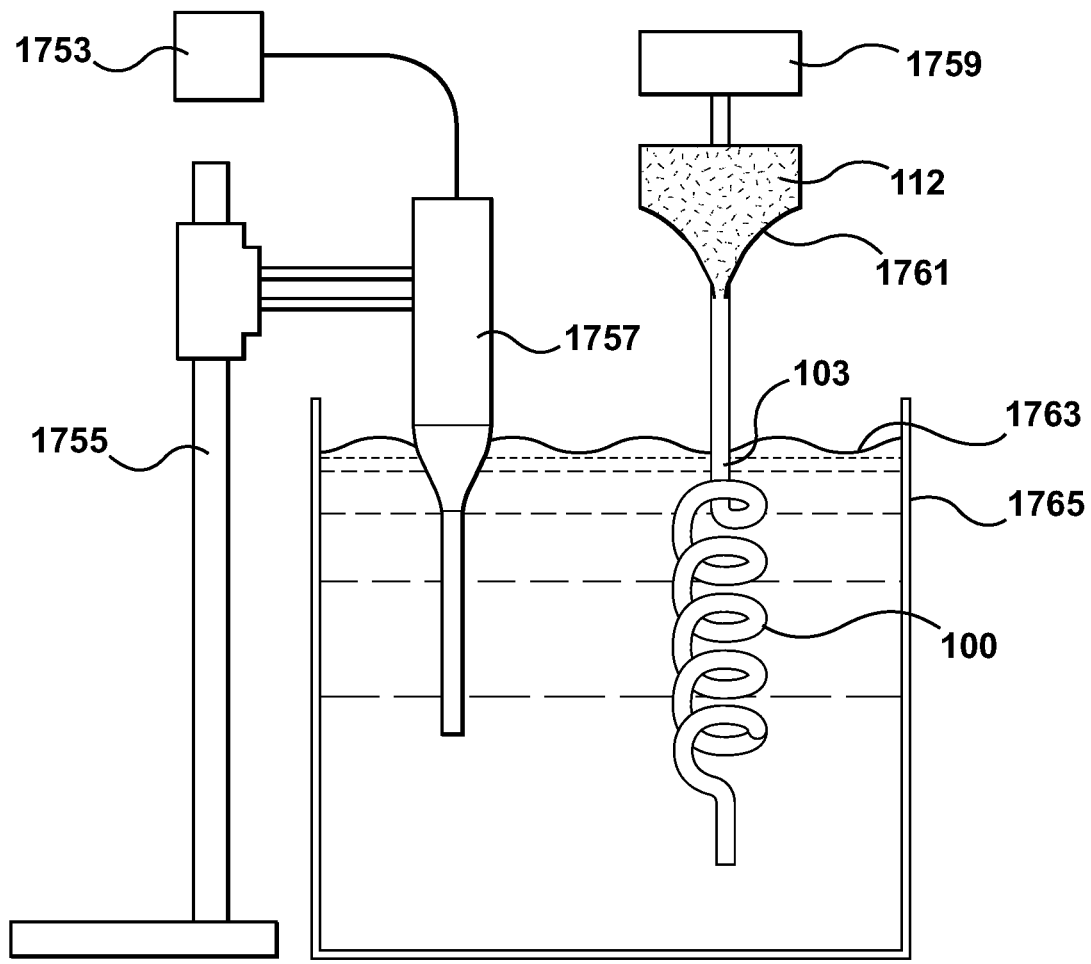
FIG. 17 is a schematic illustration of an apparatus for forward filling a drug eluting stent utilizing vibration.

Forward filling the stent may be assisted by vibration. Vibration may be applied directly or through a liquid bath. Vibration assists in moving the therapeutic substance through the lumen of the stent. FIG. 17 shows a schematic representation of an embodiment using vibration to assist drug loading. Hollow stent 100 is placed in a container 1765 filled with a liquid 1763, such as water. A hopper 1761 including a drug formulation is coupled to one end of the hollow stent 100 and the opposite end of the stent is closed. The drug formulation may be a solution or a slurry/suspension that includes the therapeutic substance or a dry therapeutic substance. A pump 1759 is coupled to hopper 1761 to push the drug formulation through lumen 103 of hollow stent 100. A sonicator 1757 or similar vibration producing device is placed in the liquid 1763. The sonicator 1757 may be held in place by a support structure 1755 and coupled to a power source 1753. While the drug formulation is being loading through lumen 103 of hollow stent 100, the sonicator 1757 vibrates liquid 1763, thereby vibrating hollow stent 100. The sonicator may be vibrated at about 20-100 kHz. It would be understood by those skilled in the art that vibration techniques may be used with other loading methods and various means to vibrate the stent may be used. For example, the sonicator 1757 or similar vibrating device may contact portions of the stent directly.

Figure 18:
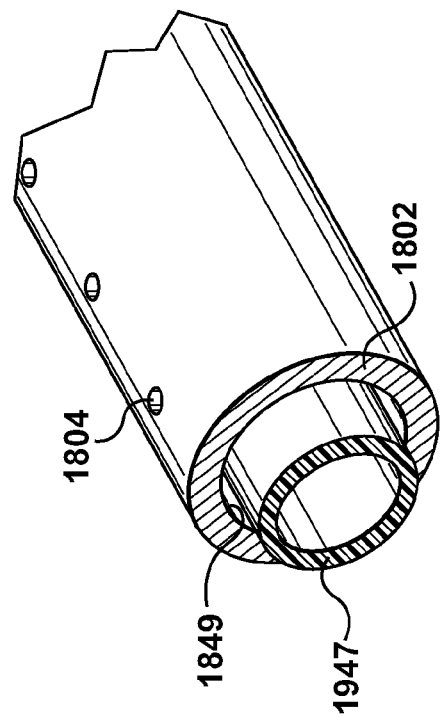
FIG. 18 is a cross-sectional view of a drug eluting stent having a biodegradable liner to assist in forward filling the stent.

Drug delivery openings 104 of hollow stent 100 are blocked or plugged during the forward fill process in order to prevent liquid 1763 from entering hollow stent 100 via openings 104, and to further minimize leakage as the therapeutic substance and solvent/dispersion medium are pumped into the lumen of the stent. In addition, vibration to forward fill a stent may be utilized to fill a formed hollow stent 100 as shown in FIG. 17 or may be utilized to fill a straight hollow tube 102 that is subsequently formed into hollow stent 100.
Drug Filling: Forward Fill Embodiments Utilizing Biodegradable Liner or Plugs In one embodiment, the stent may include a liner to assist in filling the stent with the therapeutic substance or drug and to further control the rate of drug delivery after stent implantation. More particularly, referring to the cross-sectional view of FIG. 18, stent 1800 may include a bioabsorbable/biodegradable liner 1851 that conforms to an inner surface 1849 of hollow wire 1802. In one embodiment, liner 1851 may have a thickness that ranges between 0.001-0.002 inches. Liner 1851 prevents therapeutic substance 1812 from leaking through side openings 1804 during the drug filling step of the manufacturing process. After placement of liner 1851 as described below, stent 1800 may be filled or loaded with therapeutic substance 1812 utilizing any forward fill method described herein. Regardless of the type of filling method utilized, liner 1851 ensures that therapeutic substance 1812 does not seep out or leak through openings 1804 as lumen 1803 of hollow wire 1802 is filled.

In addition to blocking openings 1804 during manufacture, liner 1851 also acts as a mechanism to control release of therapeutic substance 1812 into a body vessel after stent 1800 is implanted therein. Liner 1851 is formed from a bioabsorbable/biodegradable polymer that dissolves or breaks down within a vessel such that therapeutic substance 1812 is permitted to elute into the vessel lumen. In one embodiment, liner 1851 is formed out of polylactic acid (PLA), which is a biodegradable plastic that has been used for many years for medical uses such as biodegradable sutures. Other biodegradable polymers suitable for use in constructing liner 1851 include, for example, polyglycolic acid, collagen, polycaprolactone, hylauric acid, co-polymers of these materials, as well as composites and combinations thereof. Bioabsorbable polymers suitable for use in constructing liner 1851 include polymers or copolymers such as polylactide [poly-L-lactide (PLLA), poly-D-lactide (PDLA)], polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) or two or more polymerizable monomers such as lactide, glycolide, trimethylene carbonate, $\epsilon$-caprolactone, polyethylene glycol, caprolactone derivatives such as 4-tert-butyl caprolactone and N-acetyl caprolactone, poly(ethylene glycol)bis(carboxymethyl)ether. Each type of biodegradable polymer has a characteristic degradation rate in the body. Some materials are relatively fast bioabsorbing materials (weeks to months) while others are relatively slow bioabsorbing materials (months to years). The dissolution rate of liner 1851 may be tailored by controlling the type of bioabsorbable polymer, the thickness and/or density of the bioabsorbable polymer, and/or the nature of the bioabsorbable polymer. In addition, increasing thickness and/or density of a polymeric material will generally slow the dissolution rate of the liner. Characteristics such as the chemical composition and molecular weight of the bioabsorbable polymer may also be selected in order to control the dissolution rate of the liner.

After stent 1800 is implanted in the vessel, bioabsorbable/biodegradable liner 1851 will breakdown due to exposure to blood flowing through the vessel, thereby allowing therapeutic substance 1812 to be released at the treatment site and into the bloodstream. In comparison to an exterior bioabsorbable/biodegradable coating used for controlling release of therapeutic substance 1812 into a vessel after stent 1800 is implanted, liner 1851 is more protected during further processing steps such as crimping stent 1800 onto a balloon of a balloon catheter (not shown). Further, polymer coatings on exposed surfaces of medical devices may flake off or otherwise be damaged during delivery. In comparison, liner 1851 is protected from flaking off or otherwise being damaged during delivery since liner 1851 is inside hollow wire 102.

Figure 19:
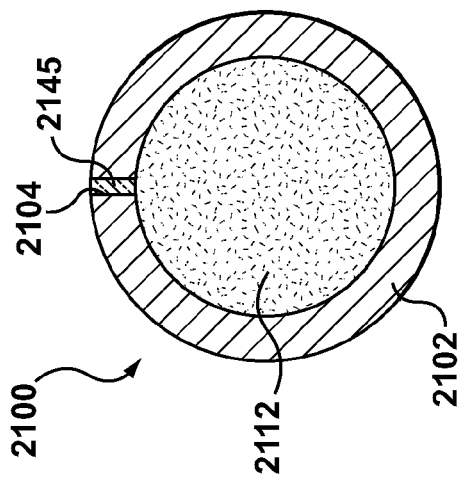
FIGS. 19 and 20 are schematic illustrations of a method utilized for forming the biodegradable liner of FIG. 18.
Figure 20:
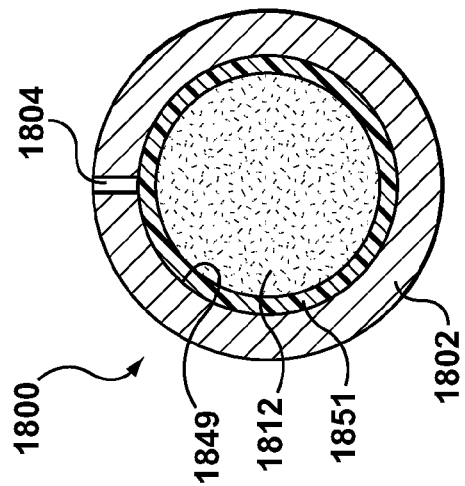

FIGS. 19 and 20 illustrate one exemplary method of manufacture for liner 1851. More particularly, in one embodiment a hollow tube 1947 of a bioabsorbable/biodegradable polymer is fed into lumen 1803 of hollow wire 1802. Hollow wire 1802 may be straight or formed into a stent configuration. Similar to balloon forming technology, tube 1947 is clamped at either end, and simultaneously internal pressure and external heat are applied so that tube 1947 blows out to form liner 1851 that confirms to inner surface 1849 of hollow wire 1802. The blowing process thus stretches and thins tube 1947 into liner 1851. Other manufacturing processes may be employed to form liner 1851, including but not limited to gas-assisted injection molding and dipping or pumping bioabsorbable/biodegradable polymer in liquid form into a hollow stent, with or without masked regions on the exterior surface of the stent.

Figure 21:
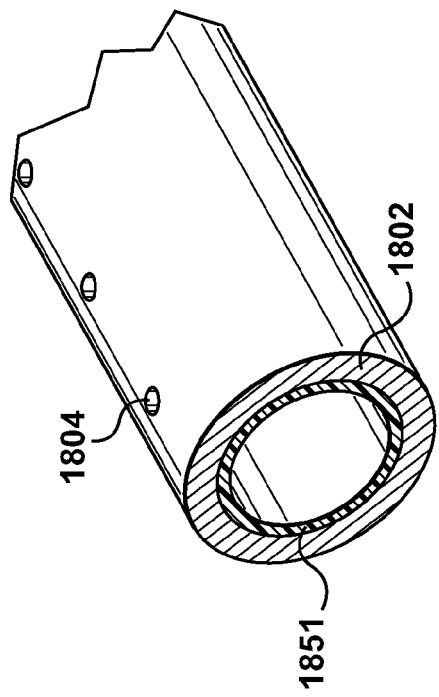
FIG. 21 is a cross-sectional view of a drug eluting stent having biodegradable plugs to assist in forward filling the stent.

Referring now to FIG. 21, another embodiment is shown in which the drug delivery openings 2104 of stent 2100 are filled with plugs 2145 of a bioabsorbable/biodegradable polymer. Similar to liner 1851 described above, plugs 2145 serve to assist in filling stent 2100 with therapeutic substance or drug 2112 and to further control the rate of drug delivery after stent implantation. Plugs 2145 substantially fill the drug delivery side openings and thus extend approximately from the outer surface to the inner surface of hollow wire 2102. Plugs 2145 may have a top surface that is flush with the outside surface of stent 2100 or may be slightly raised or bumpy. Plugs 2145 prevent therapeutic substance 2112 from leaking through the drug delivery side openings during the drug filling step of the manufacturing process. After placement of plugs 2145, stent 2100 may be filled or loaded with therapeutic substance 2112 utilizing any forward fill method described herein. In addition to blocking the drug delivery side openings during manufacture, plugs 2145 also act as a mechanism to control release of therapeutic substance 2112 into a vessel after stent 2100 is implanted because plugs 2145 are formed from a bioabsorbable/biodegradable polymer that dissolves or breaks down within a vessel such that therapeutic substance 2112 is released or emitted into the vessel lumen.

Plugs 2145 may be formed from any bioabsorbable/biodegradable polymer described above with respect to liner 1851. In one embodiment, plugs 2145 are formed from the outside surface of hollow wire 2102 and may be formed from any appropriate method, including but not limited to syringing the bioabsorbable/biodegradable polymer in liquid form into the drug delivery side openings, manually wedging solid plugs having the same profile as the drug delivery side openings into the side openings, and dipping the hollow stent into the bioabsorbable/biodegradable polymer in liquid form into hollow stent, with or without masked regions on the exterior surface of the stent.

Drug Filling: Forward Fill Embodiments Utilizing Drug Formed into Solid Rod or Cylinder In another embodiment, the therapeutic substance is formed into a rod or solid cylinder with a diameter smaller than the diameter of lumen 103 of hollow wire 102. The therapeutic substance can be formed into a solid cylinder by combining it with a binder, such as lactose powder, dibasic calcium phosphate, sucrose, corn starch, microcrystalline cellulose and modified cellulose, and combinations thereof. The therapeutic substance and binder are uniformly mixed and pressed into the desired shape, such as a rod or cylinder shape in this embodiment. The rod is then inserted into lumen 103 of the hollow wire 102 prior to the hollow wire being bent into a stent pattern, that is, while the wire is straight. The hollow wire 102 with the therapeutic substance disposed therein is then shaped into a stent form, as described above. The therapeutic substance in a solid form provides support to the hollow wire while the hollow wire is being shaped into the stent pattern.

Figure 22:
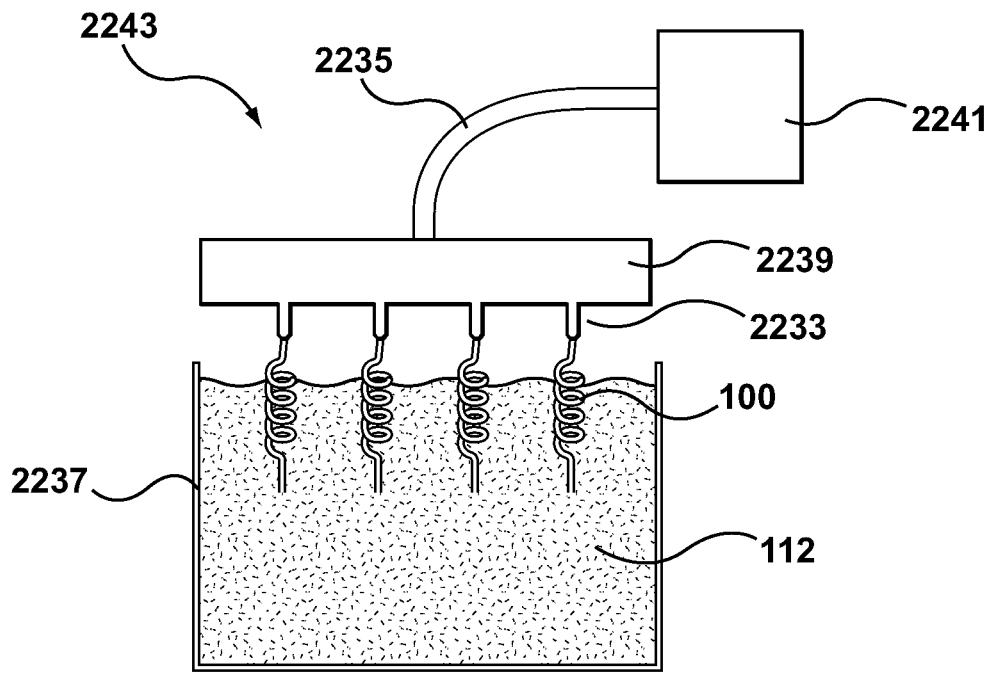
FIG. 22 is a schematic illustration of an apparatus for reverse filling a drug eluting stent utilizing a vacuum pump.

Drug Filling: Reverse and Forward Fill Embodiments Utilizing Pressure and/or Vacuum Pump FIG. 22 is a schematic illustration of an apparatus 2243 and method for loading the lumen of a hollow stent with a solution or suspension of a therapeutic substance. Apparatus 2243 includes a vacuum pump 2241, a manifold 2239, and a reservoir 2237. Reservoir 2237 is filled with a drug formulation in solution or suspension that includes therapeutic substance 112. Vacuum pump 2241 is coupled to manifold 2239 by tubing 2235 or other suitable coupling mechanisms. Manifold 2239 is coupled to first open ends 114, 114' of a plurality of hollow stents 100 using fittings 2233, or other suitable fluid coupling mechanisms, to be in fluid communication with lumenal spaces 103 of respective hollow wires 102 that form hollow stents 100. Hollow stents 100 extend from manifold 2239 into the solution or suspension filled reservoir 2237. In operation, vacuum pump 2241 draws a vacuum through manifold 2239 and lumenal spaces 103 of hollow stents 100 to draw the drug formulation through side openings 104 as well as through opposing open second ends 114, 114' of hollow stents 100. In this manner, the lumenal spaces 103 of hollow stents 100 are filled with the drug formulation.

Figure 23:
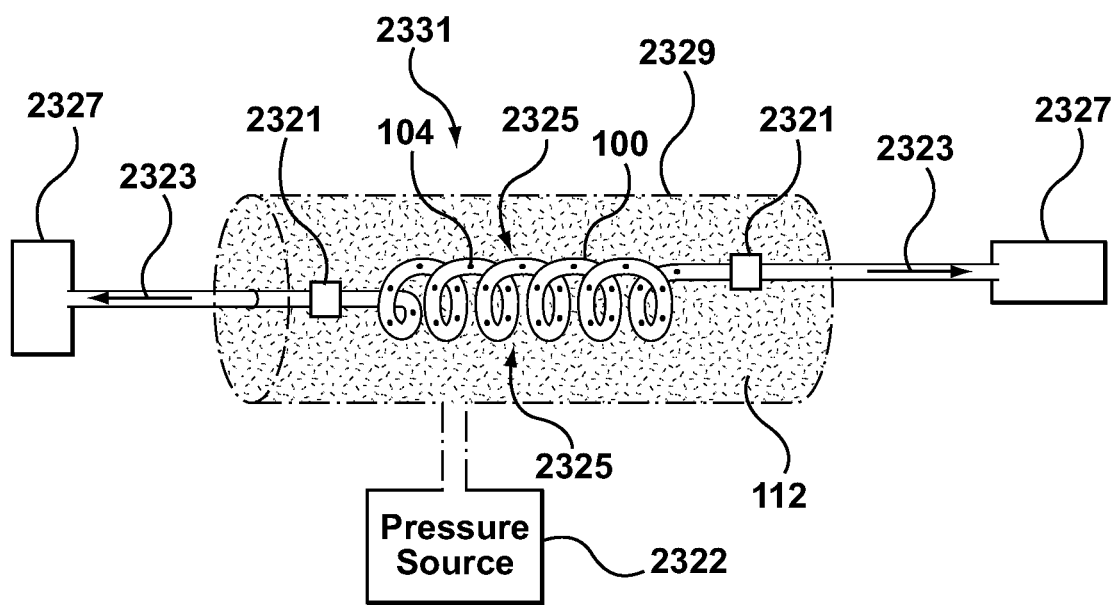
FIGS. 23 and 23A are schematic illustrations of apparatuses for reverse or forward filling a drug eluting stent utilizing vacuum pumps and a pressure differential.

FIG. 23 is a schematic illustration of an apparatus 2331 and method for loading the lumen of a hollow stent with a therapeutic substance in accordance with another embodiment hereof. Apparatus 2331 includes a pressure chamber or vessel 2329 (shown in phantom) and vacuum pumps 2327. Pressure chamber 2329 is a pressure-controlled container suitable for enclosing a hollow stent submerged within a drug suspension. A pressure source 2322 is fluidly connected to the interior of pressure chamber 2329 for controlling the pressure within chamber 2329. Other pressure chamber configurations are suitable for use herein, including for example but not limited to the apparatus of FIG. 23A described below and the packing bomb described above with respect to FIGS. 8-9.

A hollow stent is disposed in pressure chamber 2329 and a therapeutic substance 112 in suspension is provided in or supplied to the pressure chamber. The open ends of the hollow stent extend beyond pressure chamber 2329 and may be sealed to pressure chamber 2329 by compression fittings (not shown), such as but not limited to a nut and ferule combination. Vacuum pumps 2327 are coupled to lumen 103 of hollow stent 100 via respective opposing open ends 114, 114'. In one embodiment, the pressure inside pressure chamber 2329 is higher than atmospheric pressure and a resulting inward force, represented by arrows 2325, pushes or forces the suspension of therapeutic substance 112 into lumen 103 of the hollow stent through side openings 104. Simultaneously, vacuum pumps 2327 cause an outward force, represented by arrows 2323, to aid in drawing the suspension and particularly the solid particles of therapeutic substance 112 outwardly towards respective open ends 114, 114' and vacuum pumps 2327. In another embodiment, the pressure inside pressure chamber 2329 can be equilibrated with atmospheric pressure and the pressure differential caused by vacuum pumps 2327 acts to draw the solid particles of therapeutic substance 112 into the lumenal space of the stent and outwardly towards vacuum pumps 2327. Filters 2321 may be provided at either end of hollow stent 100 such that the therapeutic substance "stacks-up" against the filters to tightly pack the lumenal space 103 of the hollow stent 100 while the dispersion medium is allowed to pass through filters 2321. It would be understood by one of ordinary skill in the art that the method and apparatus described above may be varied such that a vacuum is provided along the surface of hollow stent 100 through side openings 104 and the therapeutic substance in solution or suspension may be forced inwardly into the lumenal space from the open ends 114, 114' of hollow stent 100. More particularly, the same set-up or apparatus may be utilized except that the vacuum is applied to the side openings 104 of hollow stent 100 by developing a vacuum within pressure chamber 2329. In this embodiment, the vacuum pumps 2327 would be drawing directly from pressure chamber 2329 to develop the vacuum. The open ends 114, 114' of stent 100 would be immersed in a solution or slurry/suspension of therapeutic substance and thereby be drawn or forced into the lumenal space of stent 100 due to the pressure differential. In one embodiment, the solution/suspension may be pressurized such that the vacuum from pressure chamber 2329 and the pressure applied for the solution/suspension force the solution/suspension to fill the lumenal space of stent 100.

Figure 23A:
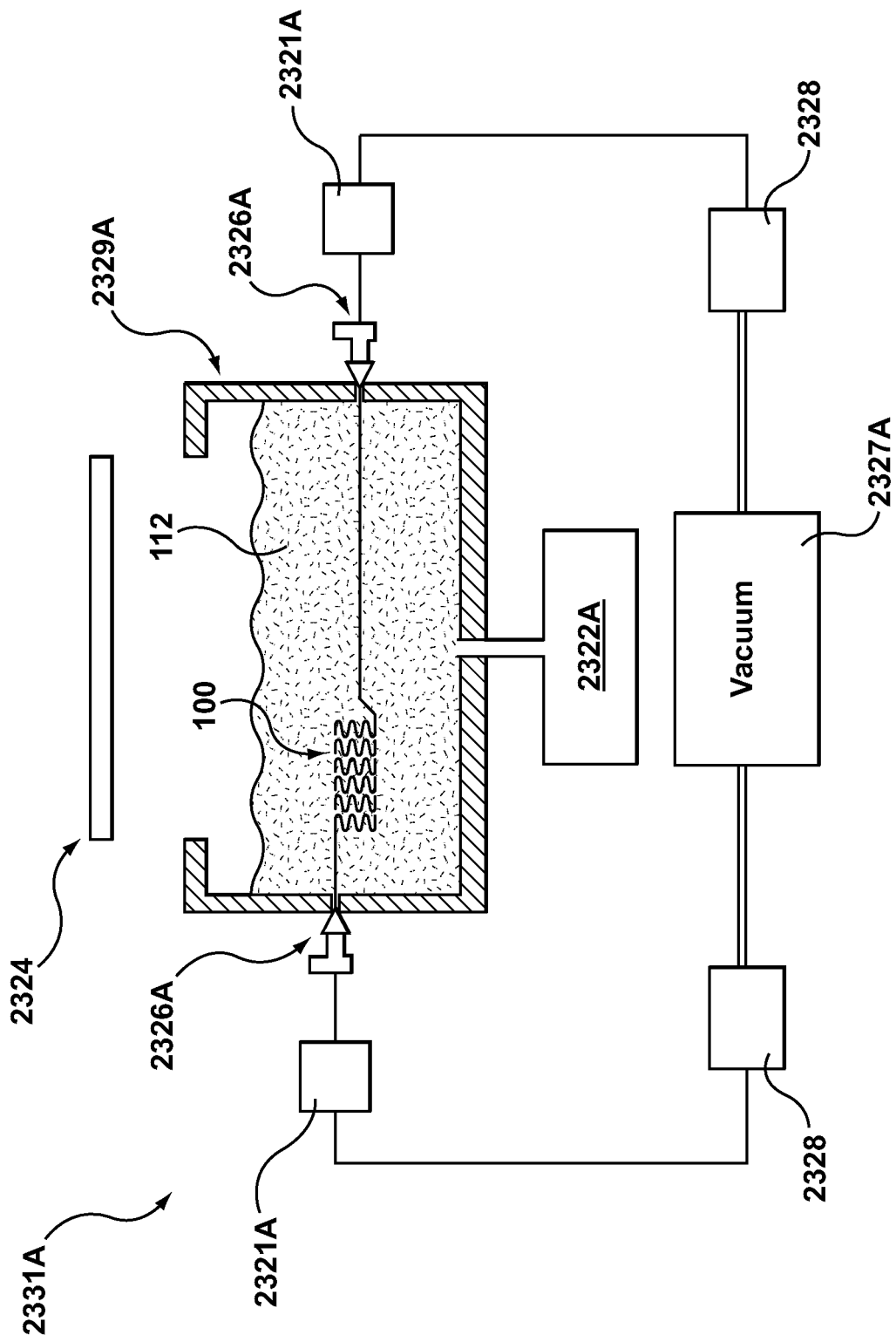

FIG. 23A illustrates another embodiment of a pressure-controlled container suitable for enclosing a hollow stent submerged within a drug suspension. Apparatus 2331A, which functions similarly to apparatus 2331 described above, includes a pressure chamber or vessel 2329A and a pressure source 2322A fluidly connected to the interior of pressure chamber 2329A for controlling the pressure within chamber 2329A. In one embodiment, pressurized gas from pressure source 2322A may assist with moving the drug suspension. Pressure chamber 2329A includes a removable sealable cap or lid 2324 that allows a hollow stent 100 to be placed into pressure chamber 2329A chamber. A hollow stent 100 is disposed in pressure chamber 2329A and a therapeutic substance 112 in suspension is provided in or supplied to the pressure chamber. The open ends of the hollow stent extend beyond pressure chamber 2329A and may be sealed to pressure chamber 2329A by compression fittings 2326A, such as but not limited to nut and ferule combinations. Frit or filters 2321A are placed in line between each end of stent 100 and a vacuum pump 2327A such that the therapeutic substance "stacks-up" against the filters to tightly pack the lumenal space 103 of the hollow stent 100 while the dispersion medium is allowed to pass through filters 2321A. Tube adapters 2328 are also placed in line between each end of stent 100 and a vacuum pump 2327A to allow change in tubing size from the frit/compression fitting to the vacuum pump. As discussed above with respect to FIG. 23, the pressure differential and vacuum pump 2327A pushes or forces the suspension of therapeutic substance 112 into lumen 103 of the hollow stent through side openings 104.

Pressure chamber and/or vacuum pumps to reverse fill or forward fill a stent may be utilized to fill a formed hollow stent 100 as shown in FIGS. 22, 23, and 23A, or may be utilized to fill a straight hollow wire or tube 102 that is subsequently formed into hollow stent 100.

Drug Filling: Reverse Fill Embodiments Utilizing Vibration

Figure 24:
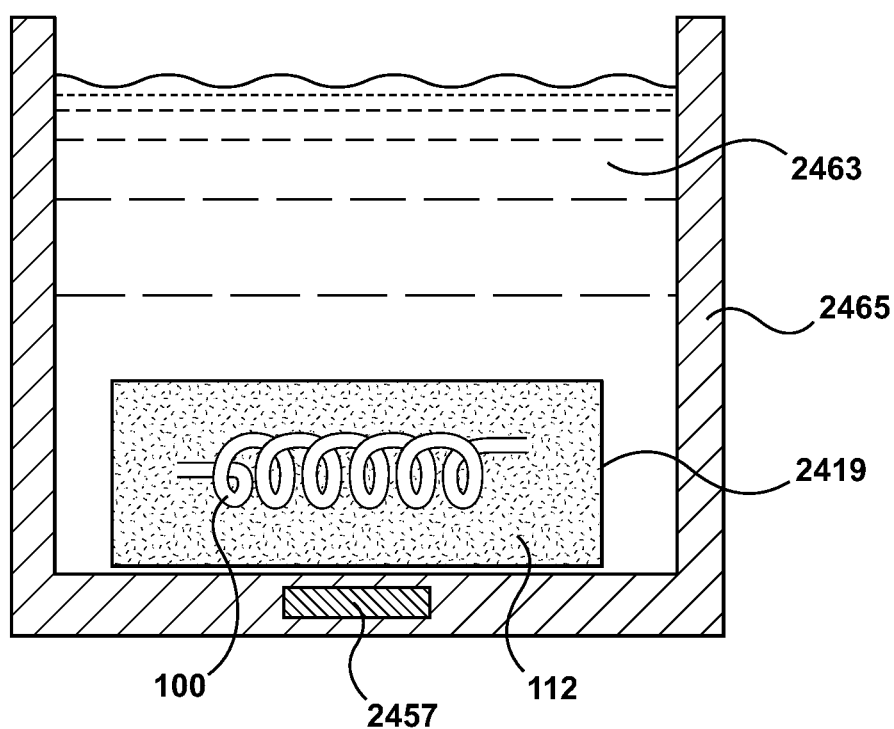
FIG. 24 is a schematic illustration of an apparatus for reverse filling a drug eluting stent utilizing vibration.

In another embodiment, vibration may be used to reverse fill hollow stent 100. Vibration may be applied to hollow stent 100 directly or through a liquid bath. Vibration assists in moving a solution or suspension of the therapeutic substance across drug delivery side openings 104 and into lumen 103 of hollow wire 102 that forms stent 100. FIG. 24 shows a schematic representation of an embodiment using an ultrasonic bath to assist in drug loading. A container or tube 2419 is filled with a drug solution or suspension having therapeutic substance 112, and hollow stent 100 in its formed configuration is submerged therein. Tube 2419 is placed within a chamber 2465 of the ultrasonic bath. Chamber 2465 is filled with a liquid 2463, such as water or other solution. Ultrasonic baths generally include an internal ultrasound generating transducer 2457 built into chamber 2465 to produce ultrasonic waves in liquid 2463 by changing size in concert with an electrical signal oscillating at ultrasonic frequency. Alternatively, an external ultrasound generating transducer such as sonication horn 1757 described above with respect to FIG. 17 may be placed into liquid 2463 to produce vibrations. Internal ultrasound generating transducer 2457 vibrates liquid 2463, thereby vibrating the drug solution or suspension into drug delivery openings 104 of hollow stent 100. In one embodiment, the drug solution or suspension is vibrated for a duration of between 1 hour and 4 hours. The internal ultrasound generating transducer 2457 may be vibrated at about 20-100 kHz. It would be understood by one of ordinary skill in the art that vibration techniques may be used with other loading methods and various means to vibrate the stent may be used. In one embodiment, ice or another cooling agent may be added to the ultrasonic bath as needed to ensure that hollow stent 100 does not warm above room temperature during the sonication.

After sonication, hollow stent 100 is removed from container 2419 with lumenal space 103 full of the drug solution or suspension, which includes therapeutic substance 112, solvent or dispersion medium, and/or any modifiers/additives such as one or more surfactants or excipients, and at least partially dried to remove a majority of the exterior solvent or dispersion medium. After drying, the exterior surface of hollow stent 100 may be coated with the same solution or suspension components, either as a layer of cast drug solution or a dried drug residue. Hollow stent 100 may further undergo a solvent extraction step as described herein and/or a stent cleaning step as described herein to remove any remaining solvent or dispersion medium from the lumenal space and/or to remove the cast layer of drug solution or drug residue from the outer surface of the stent. Vibration to reverse fill a stent may be utilized to fill a formed hollow stent 100 as shown in FIG. 24, or may be utilized to fill a straight hollow tube 102 that is subsequently formed into hollow stent 100.

Solvent Extraction: Azeotrope to Precipitate Drug

FIGS. 25-28 illustrate an embodiment in which a precipitation method is utilized to separate a drug from a solvent after a solution has been loaded into the lumenal space of hollow wire. More particularly as shown in a first step 2520 of FIG. 25 and in the cross-sectional view of FIG. 26, hollow wire 2602 of stent 2600 is first filled with a solution 2617 of therapeutic substance or drug 112 and a first solvent. Therapeutic substance 112 is soluble within the first solvent to form solution 2617. The first solvent may be a high or low capacity solvent. In one embodiment, the first solvent is tetrahydrofuran (THF), although other solvents suitable for dissolving therapeutic substance 112 may be utilized. THF is a high capacity solvent that dissolves a large amount of various drugs, such as for example sirolimus. As will become apparent by the following description, the first solvent must also be capable of forming an azeotrope with a second or precipitator solvent that is added later in the process. Stent 2600 may be filled or loaded with solution 2617 utilizing any filling method described herein, however a reverse filling method such as vibration via ultrasonic bath is preferred so that evaporation of the first solvent may occur quickly through the multiple openings 2604 spaced along the length of stent 2600.

In a second step 2521 of FIG. 25, a second or precipitator solvent is added to the lumenal space of stent 2600. The second solvent has the following characteristics in order to perform these key functions: (1) the second solvent does not dissolve therapeutic substance 112, i.e., therapeutic substance 112 is insoluble in the second solvent such that therapeutic substance 112 precipitates from solution 2617, and (2) the second solvent is miscible with the first solvent to ensure proper homogenous mixing and is capable of forming an azeotrope with the first solvent. As to the first characteristic of the second precipitator solvent listed above, it is noted that the second precipitator solvent may be referred to as a nonsolvent in that it is a substance incapable of dissolving therapeutic substance 112 within solution 2617. As to the second characteristic of the second precipitator solvent listed above, an azeotrope is a mixture of two or more liquids in such a ratio that its composition is not changed when boiled, because the resulting vapor has the same ratio of constituents as the original mixture. The second or precipitator solvent is added until the two solvents, i.e., the first solvent and the precipitator solvent, reach the azeotrope point. For example, when THF is utilized as the first solvent, hexane may be utilized as the second precipitator solvent. Various drugs, including sirolimus, are insoluble in hexane. Further, THF and hexane are miscible and form an azeotrope at 46.5% THF and 53.5% hexane by weight (w/w). Since the azeotrope point of a THF/hexane mixture requires 53.5% hexane, a large amount of hexane can be added to solution 2617 in order to ensure that therapeutic substance 112 precipitates from solution 2617. In another embodiment, ethanol may be utilized as the first solvent for dissolving the therapeutic substance and water may be utilized as the second precipitator solvent that forms an azeotrope with ethanol, as long as the therapeutic substance is insoluble in water. After precipitation, as shown in the cross-sectional view of FIG. 27, therapeutic substance 112 exists in a solid phase while the two solvents, i.e., the first solvent and the precipitator solvent, exist as a mixture 2715 in a liquid phase.

The second precipitator solvent may be added to the lumenal space of stent 2600 in any suitable method. For example, if vibration is being utilized in a reverse fill method to load hollow stent 100, the second precipitator solvent may simply be added to the ultrasound/ultrasonic bath while stent 100 is still submerged in solution 2617 and the second precipitator solvent will enter the lumenal space via the drug delivery side openings of the immersed stent. The second precipitator solvent will cause therapeutic substance 112 to precipitate from the first solvent both within the lumenal space of hollow wire 2602 and external to stent 2600. By precipitating therapeutic substance 112 out of solution 2617, the drug and the solvents are separated and a cast layer of dried drug will not form and block openings 2604 upon drying.

Referring now to a third step 2538 of FIG. 25, solvent extraction is performed to remove the two solvents, i.e., the first solvent and the precipitator solvent, which exist as liquid mixture 2715 within the lumenal space of hollow wire 2602. Stent 2600, while still immersed within mixture 2715 or removed therefrom, is placed in a vacuum oven. Temperature and pressure are controlled such that the azeotrope formed between the first solvent and the precipitator solvent becomes volatile and goes into a gaseous phase. For example, ambient pressure may be reduced to approximately 5 torr and temperature may be increased to between 30 degrees C. and 40 degrees C. for a THF-hexane to allow rapid evaporation of the solvents. The specific values necessary for temperature and pressure are dependent upon the specific solvent system selected however typical values can range between $1 \times 10^{-8}$ torr to 760 torr for pressure and 25 degrees C. to 40 degrees C. for temperature. Mixture 2715 will flash off or evaporate from stent 2600, leaving substantially only therapeutic substance 112 in solid form within the lumenal space of hollow wire 2602 as shown in the cross-sectional view of FIG. 28. Very little to no solvents remain within hollow wire 2602. Since the first solvent and the precipitator solvent formed an azeotrope, the solubility of therapeutic substance 112 does not change as mixture 2715 is evaporated but rather remains in solid form during the solvent extraction. Since the composition of an azeotrope does not change during boiling, therapeutic substance 112 will not dissolve in any remaining mixture 2715 as the azeotrope evaporates. Forming an azeotrope to precipitate a drug within a hollow tubular stent may be utilized within a formed hollow stent or may be utilized to fill a straight hollow tube that is subsequently formed into a hollow stent.

In one embodiment, the first solvent and the precipitator solvent form a positive azeotrope meaning that the combination is more volatile than the individual components. A volatile azeotrope results in a relatively low boiling point for mixture 2715 so that mixture 2715 will flash off or evaporate from stent 2600 quickly and easily. THF and hexane mentioned in the previous embodiment may be used as the first solvent and the precipitator solvent to form a positive azeotrope having a relatively low boiling point.

In another embodiment, prior to the solvent extraction step 2538 described above, water may be added to hollow stent 100 because the addition of water to a THF/hexane/Sirolimus system can create a hard shell. The hard shell may be utilized for capping stent 2600 so that drug is not lost from the inside of the stent during handling thereof.

Solvent/Dispersion Medium Extraction Step of Stent Loading Process

Referring back to FIG. 5, after the stent is filled with a drug, the second step of the drug loading process is solvent or dispersion medium extraction 538. After the lumenal space of the hollow wire 102 is filled with a drug formulation, any residual solvent/dispersion medium must be extracted from within the lumenal space such that primarily only therapeutic substance 112 or therapeutic substance 112 plus one or more excipients are located within hollow stent 100 to be eluted into the body. Thus, the net result of solvent/dispersion medium extraction is a drug, or drug and excipient, filled hollow stent devoid of appreciable lumenal residual solvent/dispersion medium. Solvent/dispersion medium extraction preferably occurs without affecting or altering the composition of therapeutic substance 112. Solvent/dispersion medium extraction is necessary to make hollow stent 100 a biocompatible implant and is desirable to ensure consistent elution of therapeutic substance 112.

Figure 5B:
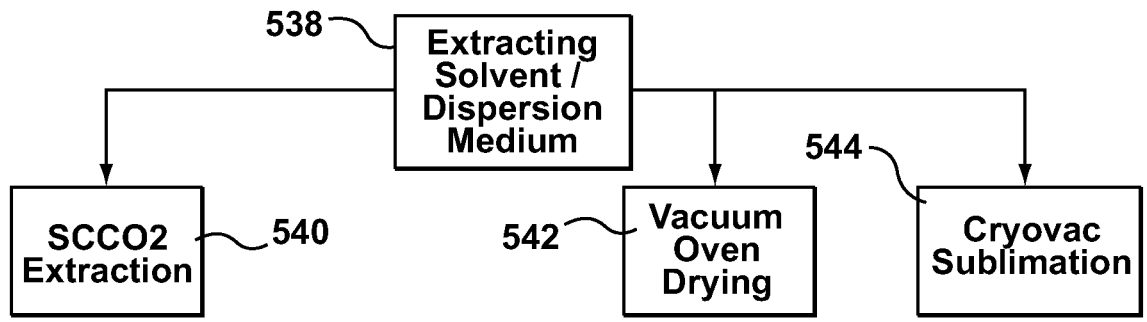
FIG. 5B is a more detailed flowchart of a solvent extraction step of FIG. 5.

FIG. 5B illustrates a more detailed flowchart of the solvent/dispersion medium extracting step 538 of the loading process, which refers to both removal of a solvent from a solution of a therapeutic material held within the luminal space of a hollow stent and removal of a dispersion medium from a slurry/suspension of a therapeutic material held within the luminal space of a hollow stent. More particularly, solvent/dispersion medium extracting step 538 is generally performed via one or more of a method of supercritical $CO_2$ extraction 540, a method of vacuum oven drying 542, and/or a method of cryovac sublimation 544. After solvent/dispersion medium extraction is performed, the lumenal space of the hollow wire is primarily filled with only drug or drug and excipient with only negligible quantities of solvent/dispersion medium. Each method is discussed in more detail below.

Solvent/Dispersion Medium Extraction: Vacuum Oven Drying Embodiment

After hollow stent 100 is filled or loaded with a drug formulation, either in solution or suspension, via any filling method described herein, the stent may be dried within a vacuum oven in order to evaporate any solvent/dispersion medium contained in the lumenal space of the hollow wire 102 and precipitate out the therapeutic material. Temperature used for drying is high enough to facilitate solvent removal, while not causing drug degradation during drying. More particularly, the stent may be placed in an oven and dried at temperatures between 25 degrees C. and 40 degrees C. and pressures between 1 torr and 760 torr for up to 24 hours to evaporate the majority of the exterior solvent/dispersion medium as well as a portion of the solvent/dispersion medium loaded with the lumenal space. After vacuum oven drying, a dried drug residue or a drug cast often remains on the exterior surface of the stent and residual solvent/dispersion medium often remains within the lumenal space.

Solvent/Dispersion Medium Extraction: Supercritical $CO_2$ Embodiment

Figure 29:
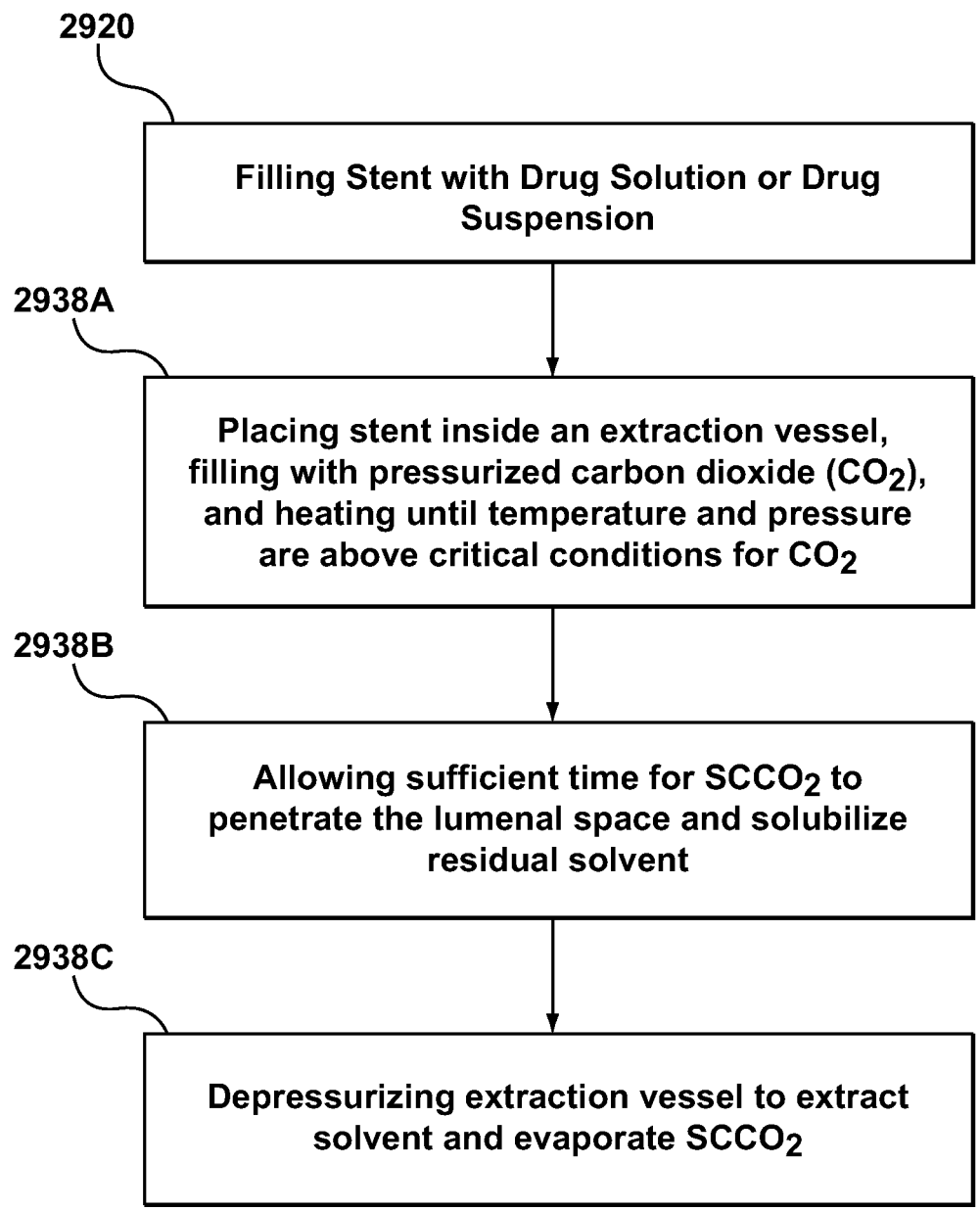
FIG. 29 is a flowchart of a method for extracting a solvent from a drug eluting stent, wherein the method utilizes static supercritical $CO_2$ extraction.
Figure 30:
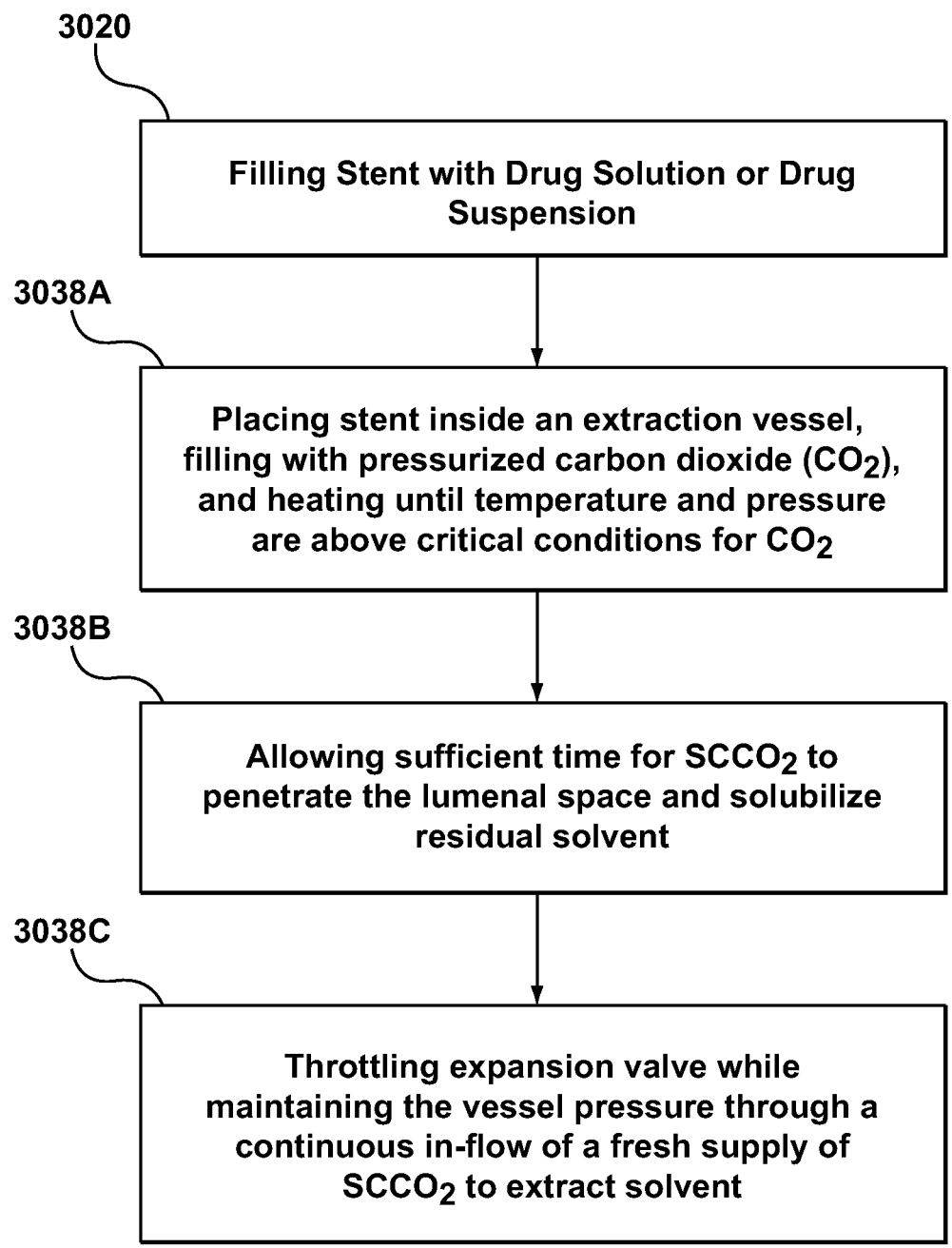
FIG. 30 is a flowchart of a method for extracting a solvent from a drug eluting stent, wherein the method utilizes dynamic supercritical $CO_2$ extraction.

With reference to FIGS. 29 and 30, two embodiments utilizing supercritical carbon dioxide ($SCCO_2$) extraction to reduce residual solvents or dispersion mediums within the lumenal space of the hollow stent to negligible quantities are illustrated. These embodiments use the properties of $SCCO_2$ to extract residual solvents or dispersion mediums while not removing the previously filled therapeutic substance/drug from the lumenal space of the stent. In a first step 2920 of a static extraction method of FIG. 29, a stent 100 is filled or loaded with a drug formulation, either in solution or suspension, via any filling method described herein such that at least the lumenal space of hollow wire 102 is filled with the drug formulation. In one embodiment, the stent may be dried within a vacuum oven prior to undergoing supercritical carbon dioxide ($SCCO_2$) extraction.

In a second step 2938A of the method of FIG. 29, the solution/suspension-filled hollow stent 100 is placed inside an extraction vessel. An extraction vessel is a pressure vessel capable of holding hollow stent 100 and capable of withstanding the temperature and pressures needed for supercritical carbon dioxide. A common configuration for an extraction vessel is a stainless steel cylinder with each end containing removable caps and fittings to allow flow of supercritical carbon dioxide, but other shapes and configurations may be utilized. The extraction vessel is heated to a temperature of between 31 degrees C. and 40 degrees C., and then filled with pressurized carbon dioxide ($CO_2$) to a pressure between 1100 psi and 9000 psi until the temperature and pressure within the extraction vessel are above critical conditions for $CO_2$ such that the supercritical carbon dioxide ($SCCO_2$) behaves as a supercritical fluid by expanding to fill the extraction vessel like a gas but with a density like that of a liquid. Supercritical fluids are by definition at a temperature and pressure greater than or equal to the critical temperature and pressure of the fluid. Carbon dioxide's critical temperature is 31.1° C. and critical pressure is 1070.9 psi (72.9 atm), so supercritical carbon dioxide ($SCCO_2$) describes carbon dioxide at a temperature above 31.1 degrees C. and at a pressure above 1070.9 psi. In a supercritical state, $CO_2$ possesses unique gas-like vapor diffusivities and liquid-like densities. Unlike conventional liquid organic solvents, $SCCO_2$ has zero surface tension and thus is capable of penetrating small voids or spaces. $SCCO_2$ also possesses solvent properties similar to organic solvents such that it is capable of solubilizing the same organic solvents used with solvents/dispersion mediums that include simple alcohols, alkanes, DCM, THF, and DMSO. In a third step 2938B of the method of FIG. 29, supercritical conditions are maintained within the extraction vessel for a sufficient period of time, such as a holding period or an equilibration time, to allow the $SCCO_2$ to penetrate the lumenal space of stent 100 and solubilize the residual solvent/dispersion medium leftover from the filling process. In one embodiment, the equilibration time is between 15 minutes and 60 minutes.

In a fourth step 2938C of the method of FIG. 29, after the $SCCO_2$ has penetrated the lumenal space of stent 100 and solubilized the residual solvent/dispersion medium, the extraction vessel is gradually depressurized to ambient pressure. The pressure reduction is controlled by an expansion valve, which includes an upstream inlet valve attached to the extraction vessel and a downstream outlet valve attached to the extraction vessel. Opening the expansion valve, which includes opening the outlet valve while keeping the inlet valve closed, allows flow of $SCCO_2$ and residual solvent/dispersion medium out from the extraction chamber and thereby reduces the pressure in the extraction vessel. The $SCCO_2$ flow occurs because the outlet of the expansion valve is at a lower pressure than the extraction chamber. In one embodiment, the outlet of the expansion valve is ambient pressure. The resulting pressure reduction or pressure drop across the expansion valve results in a volume expansion of the material flowing there-through and hence the name expansion valve. The outward flow of $SCCO_2$ and solvent/dispersion medium from the extraction vessel results in the extraction of the solvent/dispersion medium from the lumenal space of the stent with the therapeutic material in solid form being left behind. The $SCCO_2$ reverts to a gas state and evaporates away upon depressurizing. Depending on the specific solvent/dispersion medium in use as well as the nozzle geometry of the expansion valve, the extracted solvent/dispersion medium may also change to a gas state and evaporate upon exit of the expansion valve or may be extracted in a liquid state. In an embodiment, additional heating/pressurizing, holding and depressurizing steps or duty cycles, i.e., steps 2938A-2938C, may be repeatedly or cyclically employed to effect the removal of lumenal residual solvent/dispersion medium to negligible quantities.

In addition to removing residual solvent/dispersion medium from the lumenal space of the stent, $SCCO_2$ has also demonstrated a low capacity for solubilizing certain drugs such as sirolimus. Thus, $SCCO_2$ is useful for removing any drug residue located on the exterior surface of the stent after the filling process. More particularly, during the holding period described above, the $SCCO_2$ also solubilizes any exterior residual solvent and a small fraction of the exterior drug residue, resulting in a net cleaning effect on the stent exterior surface.

In a dynamic extraction method illustrated in FIG. 30, method steps 3020, 3038A and 3038B are the same as described above with respect to steps 2920, 2938A and 2938B of the method of FIG. 29. In a first step 3020, a stent is filled or loaded with a drug formulation, either in solution or suspension, via any filling method described herein. In a second step 3038A, the solution/suspension-filled stent is placed inside an extraction vessel, heated to a temperature of between 31 degrees C. and 40 degrees C., and then filled with pressurized carbon dioxide ($CO_2$) to a pressure between 1100 psi and 9000 psi until the temperature and pressure within the extraction vessel are above critical conditions for $CO_2$. In a third step 3038B, a holding period is sustained to allow the $SCCO_2$ to penetrate the lumenal space of the stent and solubilize residual solvent/dispersion medium leftover from the filling process. In one embodiment, the holding period is between 15 minutes and 60 minutes. In a fourth step 3038C of the method of FIG. 30, after the $SCCO_2$ has penetrated the lumenal space of hollow stent 100 and solubilized the residual solvent/dispersion medium, the extraction vessel is allowed to flow dynamically by throttling the expansion valve while maintaining the extraction vessel pressure through a continuous in-flow of a fresh supply of $SCCO_2$. The continuous in-flow of $SCCO_2$ is achieved by continually applying pressurized carbon dioxide to the extraction vessel and throttling the expansion valve to control the exit of material from the extraction vessel. In this embodiment, the extraction vessel is never permitted to depressurize during the extraction process because both the upstream inlet valve and the downstream outlet valve are kept open. In order to provide the fresh supply of $SCCO_2$ during dynamic extraction, the $CO_2$ pump continually adds fresh $SCCO_2$ to the extraction vessel.

In embodiments hereof, static and/or dynamic $SCCO_2$ extraction methods may be employed in one or more cycles on filled stents for between a total time of 30 and 120 minutes, at pressures between 2000 and 6000 psi. The $SCCO_2$ extraction methods reduce lumenal solvent levels to insignificant quantities. Further, in various embodiments, one or more cleaning methods described herein may be employed after the $SCCO_2$ extraction methods in order to clean the exterior of the hollow stent.

Solvent Extraction: Cryovac Sublimation Embodiment

Figure 31:
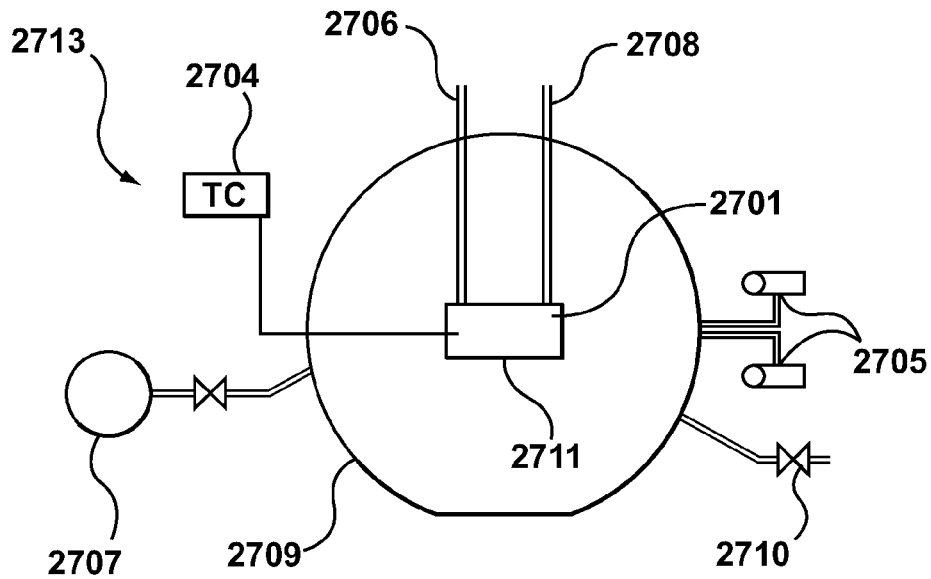
FIG. 31 is a schematic illustration of an apparatus for extracting a solvent from a drug eluting stent via cryovac sublimation.
Figure 32:
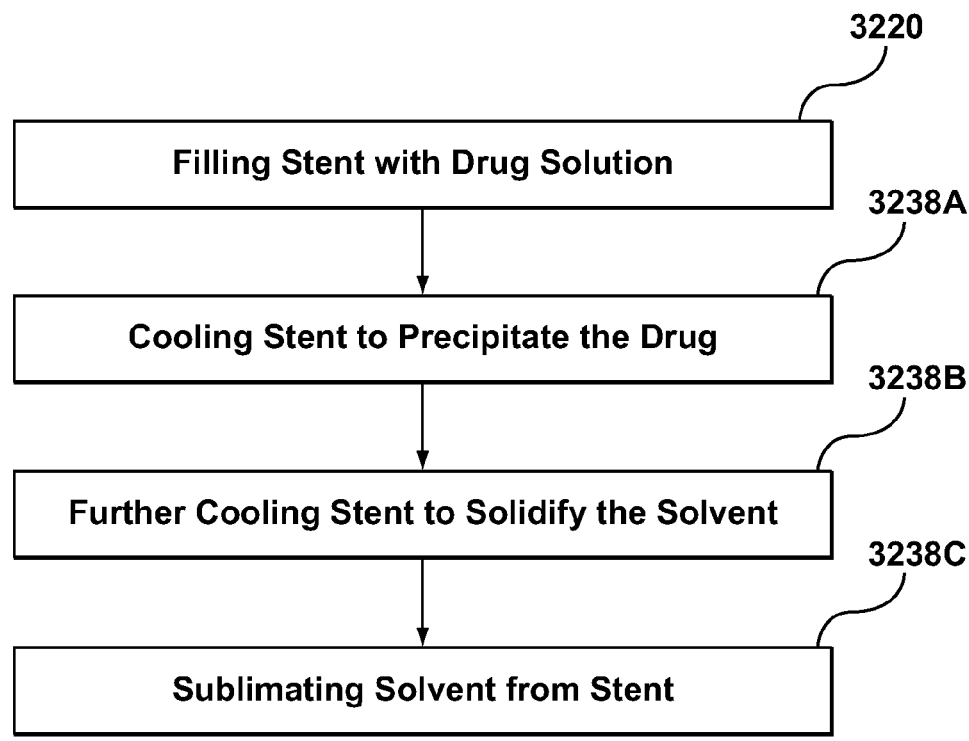
FIG. 32 is a flowchart of a method for extracting a solvent from a drug eluting stent, wherein the method utilizes the cryovac sublimation apparatus of FIG. 31.

With reference to FIGS. 31 and 32, a method is illustrated in which cryovac sublimation is utilized to extract the lumenal residual solvents in accordance with embodiments hereof. More particularly, as shown in a first step 3220 of the method of FIG. 32, a stent is filled or loaded with a solution including a therapeutic substance via filling methods described herein that are suitable for solutions such that the lumenal space of the hollow wire 102 is filled with the drug solution. In one embodiment, the drug solution includes acetonitrile and sirolimus.

After being filled, a second step 3238A of the method of FIG. 32 is to cool hollow stent 100 in order to precipitate the drug out of the solution. In particular, referring to FIG. 31, an apparatus 2713 suitable for carrying out the cryovac sublimation steps 3238A-3238C of the method of FIG. 32 is shown. One or more filled stents are placed into a sample holder 2711. In one embodiment, additional drug solution may be added to sample holder 2711 to keep the filled stents immersed within drug solution. Immersing the filled stents in drug solution prevents the outside surface of the stents from drying which may create a cast layer of dried drug over the drug delivery side openings 104 thereby blocking the openings and preventing solvent removal.

Sample holder 2711 is then loaded onto a cooling plate 2701 located within a processing chamber 2709 of apparatus 2713 and cooled via a coolant that circulates via a coolant supply line 2706 and a coolant return line 2708. In one embodiment, in order to minimize evaporation of solvent during the loading of sample holder 2711 onto cooling plate 2701, apparatus 2713 may include a special pre-conditioning step wherein pressurized inert gas, i.e., pressure above atmospheric pressure, is introduced into process chamber 2709. Examples of inert gas include but are not limited to argon, helium and nitrogen. The pre-conditioning step continues until the sample holder 2711 is loaded onto cooling plate 2701 and process chamber 2709 is closed to the atmosphere. In another embodiment, the pre-conditioning step may further continue until sample holder 2711 is cooled by cooling plate 2701 and the drug precipitates from the drug solution. The temperature and pressure of processing chamber 2709 may be controlled and manipulated such that the temperature of the drug solution is sufficient for the drug to be precipitated from the solvent. More particularly, although temperature is the key factor for precipitation, pressure control is needed in order to reach the temperature required for precipitation to occur thus both temperature and pressure of processing chamber 2709 need be controlled. The temperature of cooling plate 2701 may be controlled by the coolant temperature and how much coolant is supplied through coolant supply line 2706 and coolant return line 2708 and the pressure of processing chamber 2709 may be controlled via a vacuum pump 2707. In addition, thermocouple 2704 may be utilized for monitoring the temperature of cooling plate 2701 and pressure sensors 2705 may be utilized for monitoring the pressure within processing chamber 2709. In one embodiment, precipitation of the drug occurs at a temperature of approximately −20 degrees C. for cooling plate 2701 and a pressure of 600 torr for process chamber 2709 for a drug solution of acetonitrile and sirolimus. The cooling rate provided by cooling plate 2701 may be controlled or sufficiently slow to ensure that the precipitated drug can settle or spatially separate from the solvent prior to freezing the solvent such that entrainment of drug is minimized during solvent sublimation. The control of cooling rate is more important as the solution approaches conditions where the drug will precipitate.

After precipitation, the therapeutic substance or drug exists in a solid phase while the solvent is in a liquid phase both within the lumenal space of the stent and on an exterior of the stent. By precipitating the drug out of the solvent, the drug and the solvent are separated and a cast layer of dried drug will not form to block openings 104 upon drying. As shown in FIG. 32, a third step 3238B of the process includes further cooling stent 100 in order to solidify or freeze the solvent. Further cooling of the stent to freeze the solvent thus locks the relative position of the precipitated drug and solvent portions. In order to freeze the solvent, sample holder 2711 must reach a temperature below the melting point of the solvent. Depending on the solvent, the temperature of sample holder 2711 may be required to reach a temperature between −150 degrees C. and 0 degrees C. Examples of solvents include but are not limited to methanol, ethanol, isopropanol, acetonitrile, acetone, ethyl lactate, tetrahydrofuran, dichloromethane, hexane and water. The table below lists the melting point temperature for these representative solvents.

| Solvent | Melting Point (degrees C) |
| --- | --- |
| Methanol | −97 |
| Isopropanol | −89 |
| Ethanol | −114 |
| Acetone | −95 |
| Acetonitrile | −45 |
| Ethyl Lactate | −26 |
| Tetrahydrofuran | −108 |
| Hexane | −95 |
| Dichloromethane | −97 |
| Water | 0 |

After the solvent has been solidified, a fourth step 3238C of the method of FIG. 32 is to sublimate the frozen solvent from the stent. Sublimation is a phase transition of a substance from the solid phase to the gas phase without passing through an intermediate liquid phase. More particularly, a strong vacuum in the order of 1.0 E−3 to 1.0 E−8 Torr may be applied on processing chamber 2709 via vacuum pump 2707 so that the solvent sublimates and leaves behind only solid drug in the lumenal space of the stent. After solvent removal, the temperature and pressure of processing chamber 2709 is increased to atmospheric conditions and the stents may be removed from apparatus 2713.

In one example, a hollow stent was sonicated for more than one hour in order to reverse fill the stent with a solution of sirolimus and acetonitrile. After filling the stent with drug solution, the stent was placed into sample holder 2711 and additional drug solution was added to completely immerse the filled stent. The sample holder was then placed onto cooling plate 2701. Processing chamber 2709 was then evacuated to 600 torr and cooling plate 2701 cooled rapidly to approximately −17 degrees C. The rate of cooling was then controlled to approximately 3 degree C. per minute until precipitation of the drug and solidification of the solvent was observed. Drug precipitation began about −20 degrees C. and solidification of the solvent was observed about −30 degrees C. Processing chamber 2709 was then evacuated to less than $1 \times 10^{-3}$ torr and cooling plate 2701 cooled to approximately −45 degrees C. Cooling plate 2701 was then allowed to warm at an approximate rate of 0.5 degrees per minute with process chamber 2709 continually evacuated. Sample holder 2711 was removed after approximately 45 minutes with the temperature of cooling plate 2701 at approximately −20 degrees C. As a point of reference, the temperature of cooling plate 2701 and the temperature of the sample may not be the same. The difference in temperature is due to the design of the cooling plate, location of the thermocouple, location of the sample holder, and location of the coolant feed and return lines among other factors. In this example, cooling plate 2701 was constructed of copper and had a large area in comparison to sample holder 2711. Thermocouple 2704 was located near one edge of cooling plate 2701 and cooling holder 2711 was located near the center of cooling plate 2701. Coolant supply line 2706 and coolant return line 2708 were directed to contact cooling plate 2701 near the center. In this configuration, the indicated temperature of cooling plate 2701 from thermocouple 2704 would result in a warmer temperature than sample holder 2711. Therefore the rapid cooling of cooling plate 2701 to approximately −17 degrees C. during the cooling step also means the sample holder and therefore the drug solution was at a cooler temperature. Similarly, the observed solidification of the solvent at and indicated temperature of −30 degrees C. of cooling plate 2701 means sample holder 2711 and also the sample was at a cooler temperature. Given that the melting point of acetonitrile is −45 degrees C., the temperature offset between cooling plate 2701 and the samples was approximately 15 degrees C.

In one embodiment, vibratory energy may be applied to apparatus 2713 at any point in the process in order to promote removal of the solvent. During the precipitation and subsequent solvent freezing steps, the drug and solvent may separate into distinct areas where a volume of drug is surrounded by frozen solvent or visa versa. If a volume of frozen solvent is surrounded by drug the trapped solvent may not sublimate. The addition of vibratory energy may move the drug such that the drug no longer completely surrounds the solvent allowing sublimation. Such vibratory energy may be applied via piezoelectric transducers, oscillating magnets, or any suitable technology compatible with cryogenic temperatures and high vacuum processes.

Stent Cleaning Step of Stent Loading Process

With reference to the method depicted in FIG. 5, after the solvent is extracted from the lumenal space of the stent, a third step of the drug loading method is stent cleaning 546. The above-described methods employed to fill a hollow stent with a drug formulation will typically result in all exterior surfaces of the stent, including lumenal, ablumenal, inter-strut and inter-crown surfaces, being coated with the drug formulation used to fill the stent. Further, even after the solvent extraction step, exterior drug residue may still be present on one or more exterior surfaces of the stent. All exterior surfaces of the stent should be substantially free of drug in areas where drug delivery side openings are not present. Preferably, the stent cleaning process removes the exterior drug residue without physical manipulation of the stent and without disturbing the drug load inside the lumenal space of the stent.

Figure 5C:
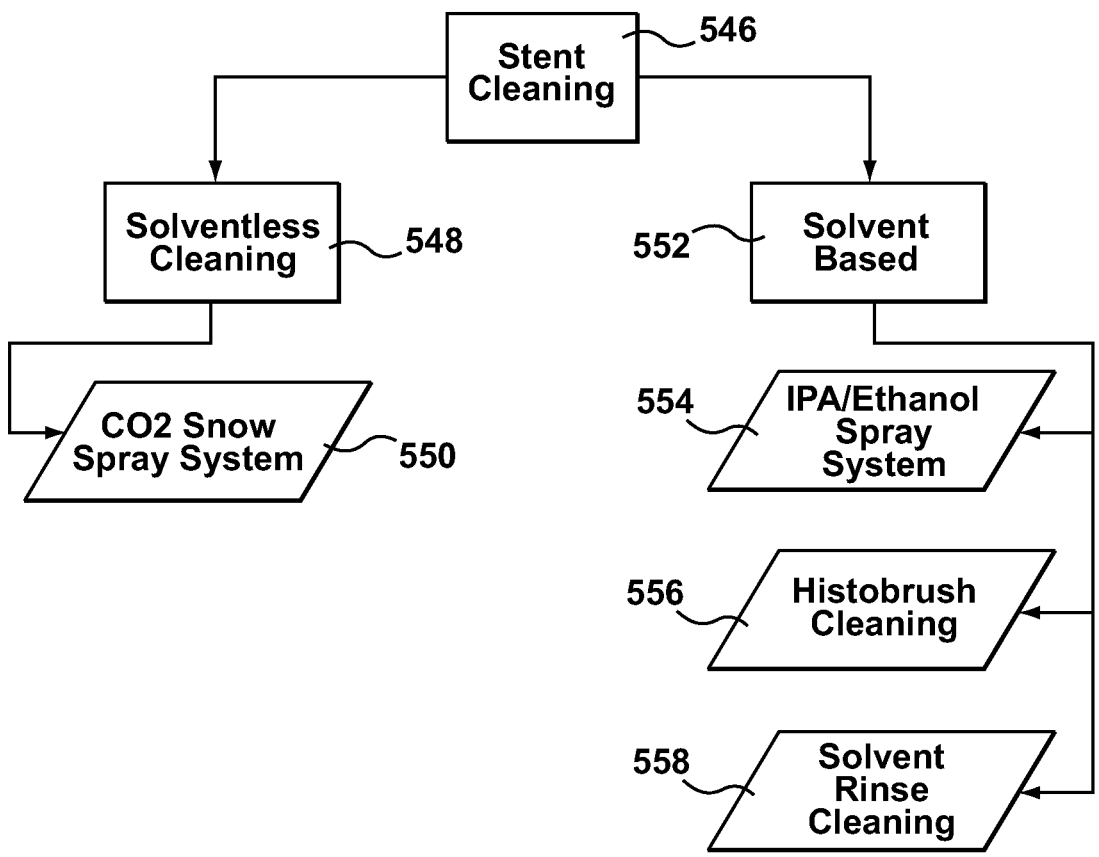
FIG. 5C is a more detailed flowchart of a stent cleaning step of FIG. 5.

FIG. 5C illustrates a more detailed flowchart of stent cleaning 546 of the drug loading process. More particularly, stent cleaning 546 may be performed by one or more of a solventless cleaning method 548, such as a method 550 utilizing a $CO_2$ dry ice snow sprayer, and/or a solvent-based cleaning method 552, including a solvent-based spray method 554, a mechanical manipulation cleaning method 556 utilizing a histobrush, and/or a solvent-based rinse method 558. Any combination of the aforementioned cleaning methods can be employed to clean the stent. The selection of cleaning method(s) may be governed by factors such as the drug formulation components, the tenaciousness of the dried components on the stent surface, the degree of unwanted drug removal from within the stent as a result of cleaning, and the degree of unwanted solvents being trapped within the stent lumen. Each method is discussed in more detail below.

Stent Cleaning without Solvent

In one embodiment a $CO_2$ spray cleaning system, also known as a $CO_2$ dry ice snow sprayer, is used for targeted removal of exterior drug residue. A suitable $CO_2$ spray cleaner is available from Applied Surface Technologies however additional modifications are necessary for use with stents. A $CO_2$ spray cleaning system takes high purity, liquid $CO_2$ and expands it at high velocity across a specially designed orifice-expansion nozzle. Both a temperature and pressure drop occurs with the expansion, thereby converting the liquid $CO_2$ into solid fine particulate $CO_2$ also known as dry ice snow. After expansion, the high velocity dry ice snow is directed towards the area of the stent containing the drug residue. Dry ice contacting the surface of the stent will cause a decrease in temperature at the stent surface followed by condensation of water vapor from the surrounding air. Continued application of the dry ice subsequently causes the condensed water to freeze. The frozen water effectively shields the stent surface from further cleaning by the dry ice. A modification to minimize the frozen water from forming is the addition of an enclosure to heat the stents. Furthermore In addition, the enclosure may be purged with an inert gas such as argon or nitrogen to minimize the amount of water vapor present. Cleaning of the stent surface is caused by the momentum transfer of the dry ice snow to the drug residue, akin to bead blasting. After contact with the stent, the dry ice snow particles are heated by the ambient temperature and the $CO_2$ eventually reverts back to the gas state. The net effect is a solvent-less cleaning process that removes exterior drug residue from the stent.

Stent Cleaning with Solvent-Based Spray Systems

A solvent spray system is designed around an ejector system, wherein air or nitrogen serving as the motive fluid entrains a solvent and atomizes the solvent into fine droplets or mist. The mist is directed at the stent with a high velocity. Depending on the solvent utilized in the spray system, the high velocity mist dissolves or displaces the drug formulation residue from the stent exterior. Various ejector systems may be utilized. An exemplary ejector system may be a nitrogen pen or airbrush, commonly used for blow-off of dust particles, connected to a small reservoir of solvent.

The solvent utilized in the solvent spray system is selected to minimize the amount of drug dissolution, and subsequent removal, from the lumenal space of the stent. Thus, solvents are chosen based on a limited ability or inability to solubilize the drug. Examples of solvents with a limited ability to solubilize various therapeutic agents, including sirolimus, include but are not limited to ethanol, isopropyl alcohol, butanol, and combinations of these alcohols with water at any mass ratio. The addition of water serves to suppress the solubilizing potential of these simple alcohols for therapeutic agents such as sirolimus that are insoluble in water. When using low drug solubility solvents, the exterior drug formulation residue is removed primarily by dissolution, followed by displacement due to the spray velocity. Examples of solvents with an inability to solubilize various therapeutic agents, including sirolimus, include but are not limited to water and simple alkanes (C5 to C10). When using non-drug solubilizing solvents, the exterior drug formulation residue is removed primarily by displacement due to the spray velocity.

Stent Cleaning with Mechanical Manipulation via Histobrush

Figure 33:
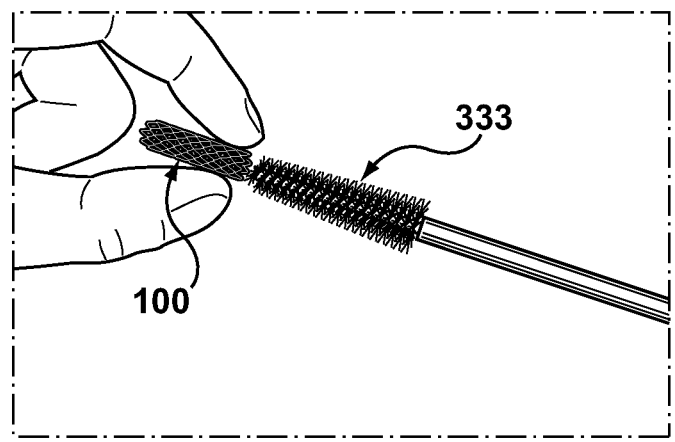
FIGS. 33 and 34 are images of cleaning the exterior surface of a stent via a histobrush.
Figure 34:
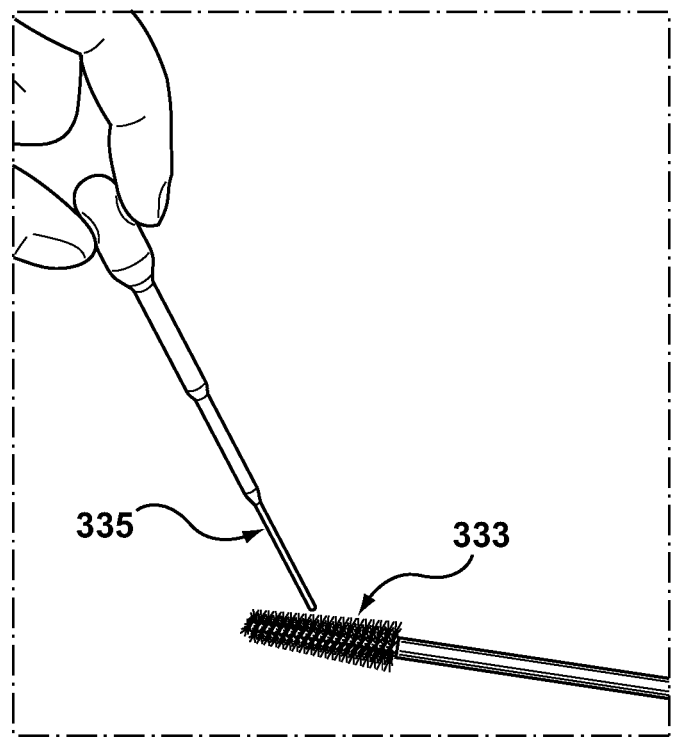

FIG. 33 illustrates another embodiment of stent cleaning in which the exterior surface of the stent is cleaned by mechanical manipulation via a histobrush 333. The histobrush brush method is manual and involves a high degree of stent handling. The user must clean the stent vigorously enough to remove all external contaminants while ensuring the mechanical integrity is not compromised during the cleaning process. As shown in FIG. 34, a solvent 335 may be added to the brush to assist in cleaning however excess solvent can remove drug from the internal portion of the stent and/or add residual solvent, resulting in a large amount of variability to the drug loading procedure.

Stent Cleaning with Solvent-Based Rinse Systems

Solvent rinse cleaning systems involve the complete immersion or dipping of hollow stent 100 in a solvent system that has limited or no ability to dissolve the drug or drug and excipients. Solvent rinse cleaning systems must tightly control the time the stent is fully immersed. Vortexing, mixing, swirling, or other means of gross fluid agitation may also be employed to shear the bulk fluid across the stent surface, thereby cleaning the stent exterior.

The solvent utilized in the solvent rinse system should minimize the amount of drug dissolution, and subsequent removal, from the lumenal space of hollow stent 100. Thus, solvents are chosen based on a limited ability or inability to solubilize the drug. Examples of solvents with a limited ability to solubilize various therapeutic agents, including sirolimus, are not limited to ethanol, isopropyl alcohol, butanol, and combinations of these alcohols with water at any mass ratio. The addition of water serves to suppress the solubilizing potential of these simple alcohols for therapeutic agents such as sirolimus that are insoluble in water. When using low drug solubility solvents, the exterior drug formulation residue is removed primarily by dissolution, followed by displacement due to the gross fluid agitation. Examples of solvents with an inability to solubilize various therapeutic agents, including sirolimus, include are but not limited to water and simple alkanes (C5 to C10). When using non-drug solubilizing solvents, the exterior drug formulation residue is removed primarily by displacement due to the gross fluid agitation.

Exemplary Combinations/Processes

In summary, a drug eluting stent such as hollow stent 100 may be loaded with a drug by a method that includes three main portions or steps as illustrated in FIG. 5, including a drug filling step 520, a solvent extracting step 538, and a stent cleaning 546. Various methods for each of the three main steps of the drug loading process are described herein, and it will be apparent to one of ordinary skill in the art that a complete loading process in accordance with embodiments hereof may include one or more types of drug filling, one or more types of solvent extraction, and one or more types of stent cleaning, and that the methods described herein may be utilized in various combinations.

Figure 35:
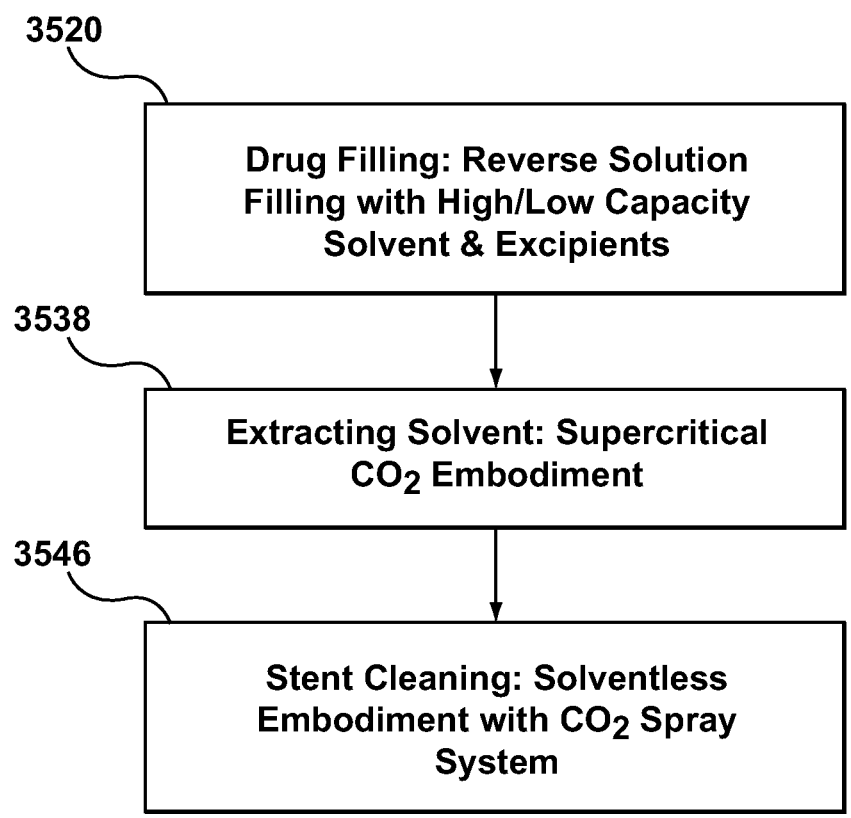
FIGS. 35, 36, and 37 are flowcharts illustrating various combinations of methods described herein for drug filling, solvent extraction, and stent cleaning.

For example, FIG. 35 illustrates one exemplary combination of apparatus and methods described herein for drug filling, solvent extraction, and stent cleaning. For a drug filling step 3520, the hollow stent 100 is reversed filled utilizing vibration/sonication as described above, for e.g., with reference to the apparatus of FIG. 24. The drug is dissolved in a high and/or low capacity solvent having one or more excipients. For a solvent extraction step 3538, supercritical carbon dioxide ($SCCO_2$) extraction is utilized to reduce the lumenal, residual solvents down to negligible quantities. A static $SCCO_2$ extraction method such as that described with reference to FIG. 29 may be utilized, or a dynamic $SCCO_2$ extraction method such as that described with reference to FIG. 30 may be utilized. Lastly, the stent is cleaned via a cleaning step 3546 that utilizes a $CO_2$ dry ice snow spray system as described above.

Figure 36:
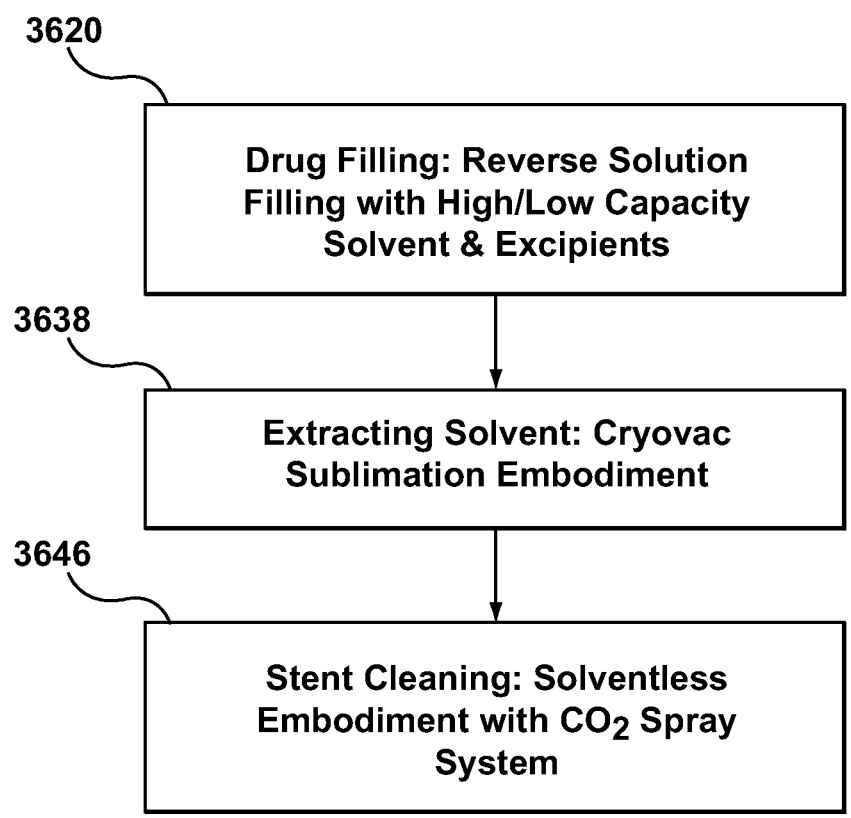

FIG. 36 illustrates another exemplary combination of apparatus and methods described herein for drug filling, solvent extraction, and stent cleaning. For a drug filling step 3620, the stent is reversed filled utilizing vibration/sonication as described above, for e.g., with reference to the apparatus of FIG. 24. The drug is dissolved in a high capacity solvent having one or more excipients, including at least urea. For a solvent extraction step 3638, cryovac sublimation as described herein within reference to FIGS. 31 and 32 is utilized to reduce the lumenal, residual solvents down to negligible quantities. Lastly, the stent is cleaned via a cleaning step 3646 that utilizes a $CO_2$ dry ice snow spray system as described above.

Figure 37:
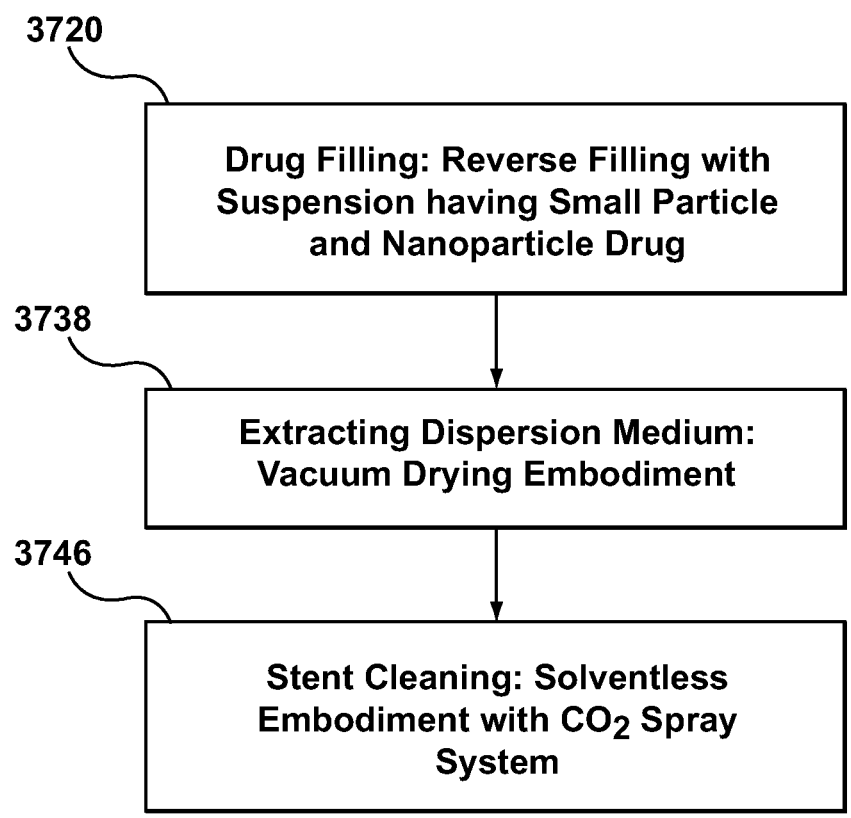

FIG. 37 illustrates another exemplary combination of the apparatus and methods described herein for drug filling, solvent extraction, and stent cleaning. For a drug filling step 3720, the stent is reversed filled utilizing vibration/sonication as described above, for e.g., with reference to the apparatus of FIG. 24. The drug is suspended in a solvent to form a slurry/suspension, and the size of the drug particles are preferably in the nanometer range. For a solvent extraction step 3738, the stent is dried within a vacuum oven in order to evaporate any solvent contained in the lumenal space of the hollow wire. Lastly, the stent is cleaned via a cleaning step 3746 that utilizes a $CO_2$ dry ice snow spray system as described above.

The above described combinations for drug filling, solvent extraction, and stent cleaning are for exemplary purposes only. It will be apparent to one of ordinary skill in the art that various combinations of the above described methods may be utilized herein for loading a drug eluting stent.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. An apparatus for loading a therapeutic substance within a lumenal space of a hollow wire having a plurality of side openings that forms a hollow stent comprising:
    upper and lower segments that mate along longitudinally-extending surfaces to form a cylindrical structure, the cylindrical structure including
    a reservoir for containing a drug suspension including the therapeutic substance and a dispersion medium,
    a loading compartment for securing at least one hollow structure therein that is to be filled with the therapeutic substance, the loading compartment being positioned downstream of and in fluid communication with the reservoir,
    a restraining plate positioned downstream of the loading compartment that allows flow of the dispersion medium therethrough while retaining the therapeutic substance upstream thereof within the hollow structure, and
    a sump chamber positioned downstream of the restraining plate that captures and contains the dispersion medium that passes through the restraining plate.

2. The apparatus of claim 1, wherein the hollow structure is a plurality of straight hollow wires and the loading compartment includes a plurality of grooves each of which is configured to hold a respective straight hollow wire to be filled with the therapeutic substance.

3. The apparatus of claim 1, wherein the hollow structure is a hollow stent and the loading compartment is cylindrical and sized to hold the hollow stent.

4. The apparatus of claim 1, wherein the upper and lower segments are equal halves of the cylindrical structure.

5. The apparatus of claim 1, wherein the reservoir is wedge-shaped.

6. The apparatus of claim 1, wherein the restraining plate is formed from sintered glass.

7. The apparatus of claim 1, wherein the loading compartment includes a rubber coating to prevent leaking of the drug suspension.

8. The apparatus of claim 1, further comprising:
    at least one screw cap for holding the two segments together in the cylindrical configuration.

9. A method of loading a therapeutic substance within a lumenal space of a hollow wire having a plurality of side openings that forms a hollow stent, the method comprising the steps of:
placing at least one hollow structure within a loading compartment of a loading apparatus;
filling a reservoir of the loading apparatus with a drug suspension including the therapeutic substance and a dispersion medium;
placing the loading apparatus into a centrifuge rotor;
applying a high G centrifugal force to drive the drug suspension into a lumenal space of the hollow structure, whereby the therapeutic substance packs within the lumenal space of the hollow structure as the therapeutic substance is separated from the dispersion medium that passes through a downstream restraining plate of the loading apparatus and is captured within a downstream sump chamber of the loading apparatus; and
removing the hollow structure from the loading apparatus when the lumenal space is substantially full of the therapeutic substance.

10. The method of claim 9, wherein the step of placing at least one hollow structure includes placing a plurality of straight hollow wires within a plurality of grooves formed in the loading compartment.

11. The method of claim 9, wherein the step of placing at least one hollow structure includes placing a hollow stent into the loading compartment, wherein the loading compartment is cylindrically shaped to hold the hollow stent.

12. The method of claim 11, further comprising:
inserting a rod through the hollow stent to secure the stent in place during the filling step.

13. The method of claim 9, wherein the loading apparatus includes upper and lower segments that mate along longitudinally-extending surfaces to form a cylindrical structure and the loading apparatus is closed by sandwiching at least one hollow structure between the upper and lower segments.

14. The method of claim 13, wherein the step of filling the reservoir of the loading apparatus with the drug suspension includes injecting the drug suspension through a rubber diaphragm of a screw cap that holds the upper and lower segments together in the cylindrical configuration.

15. The method of claim 9, wherein the reservoir of the loading apparatus is wedge-shaped.

16. The method of claim 9, wherein the restraining plate of the loading apparatus is formed from sintered glass.

17. The method of claim 9, wherein the loading compartment of the loading apparatus includes a compliant rubber coating to prevent leaking of the drug suspension.

18. The method of claim 9, wherein the drug suspension also includes an excipient to assist in elution of the therapeutic substance, wherein the excipient and therapeutic substance are packed within the hollow structure when the high G centrifugal force is applied.

19. A method of loading a therapeutic substance within a lumenal space of a hollow wire having a plurality of side openings that forms a hollow stent, the method comprising the steps of:
placing at least one hollow structure within a loading compartment of a loading apparatus;
filling a reservoir of the loading apparatus with a drug solution including the therapeutic substance dissolved within a solvent;
placing the loading apparatus into a centrifuge rotor;
applying a high G centrifugal force to drive the drug solution into a lumenal space of the hollow structure, whereby the drug solution fills the lumenal space of the hollow structure; and
removing the hollow structure from the loading apparatus when the lumenal space is substantially full of the drug solution.

20. The method of claim 19, further comprising:
the step of extracting the solvent from the lumenal space of the filled hollow structure while the therapeutic substance remains within the hollow structure such that the hollow structure is thereby loaded with the therapeutic substance, wherein the hollow structure loaded with the therapeutic substance is one of a hollow stent and a hollow wire that is subsequently formed into a hollow stent.

* * * * *